(12) United States Patent
Fischell et al.

(10) Patent No.: US 9,724,533 B1
(45) Date of Patent: Aug. 8, 2017

(54) TRANSCRANIAL MAGNETIC STIMULATION DEVICE FOR THE TREATMENT OF MIGRAINE HEADACHES

(71) Applicant: ENEURA, INC., Sunnyvale, CA (US)

(72) Inventors: Robert E. Fischell, Dayton, MD (US); David R. Fischell, Fair Haven, NJ (US); Leopold Rolih, San Jose, CA (US); Michael Graves, San Francisco, CA (US); Joseph P. Fredrick, Palo Alto, CA (US); Stanley P. Woods, Cupertino, CA (US); Richard Barthel, Brooklyn Center, MN (US)

(73) Assignee: Eneura, Inc., Sunnyvale, CA (US)

( * ) Notice: Subject to any disclaimer, the term of this patent is extended or adjusted under 35 U.S.C. 154(b) by 0 days.

(21) Appl. No.: 15/347,302

(22) Filed: Nov. 9, 2016

Related U.S. Application Data

(63) Continuation of application No. 15/346,148, filed on Nov. 8, 2016, which is a continuation-in-part of application No. 14/275,927, filed on May 13, 2014, now Pat. No. 9,526,912.

(51) Int. Cl.
*A61N 2/00* (2006.01)
*A61N 2/02* (2006.01)

(52) U.S. Cl.
CPC .............. *A61N 2/008* (2013.01); *A61N 2/02* (2013.01)

(58) Field of Classification Search
CPC .......... A61N 2/00; A61N 2/002; A61N 2/004; A61N 2/006; A61N 2/008; A61N 2/02
USPC ........................................................ 600/9–15
See application file for complete search history.

(56) References Cited

U.S. PATENT DOCUMENTS

| | | | |
|---|---|---|---|
| 5,116,304 A | 5/1992 | Cadwell | |
| 5,159,258 A | 10/1992 | Kolvites | |
| 5,406,188 A | 4/1995 | Myslinski et al. | |
| 6,132,361 A | 10/2000 | Epstein et al. | |
| 6,402,678 B1 | 6/2002 | Fischell et al. | |
| 8,125,186 B2 | 2/2012 | Carkner | |
| 8,262,556 B2 | 9/2012 | Fischell et al. | |

OTHER PUBLICATIONS

Barker, A.T., et al.; "Non-invasive magnetic stimulation of human motor cortex"; The Lancet, vol. 325, Issue 8437, pp. 1106-1107, May 11, 1985.
Pelka, R.B, et al.; "Impulse magnetic-field therapy for migraine and other headaches: A double-blind, placebo-controlled study"; Medicine Advances in Therapy; vol. 18, No. 3, 101-109; May/Jun. 2001.
Boroojerdi, B., et al.; "Reduction of human visual cortex excitability using 1-Hz transcranial magnetic stimulation"; Neurology; vol. 54 No. 7; pp. 1529-1531; Apr. 11, 2000.

*Primary Examiner* — John Lacyk
(74) *Attorney, Agent, or Firm* — Rosenberg, Klein & Lee

(57) ABSTRACT

A transcranial magnetic stimulation (TMS) device has at least one capacitor. A charging circuit charges the capacitor. The TMS device includes a magnetic coil for delivering magnetic pulses to a person's body. A bleed resistor is within the TMS device to minimize forces applied to the bleed resistor where the bleed resistor is aligned with magnetic field lines generated by the magnetic pulses.

10 Claims, 14 Drawing Sheets

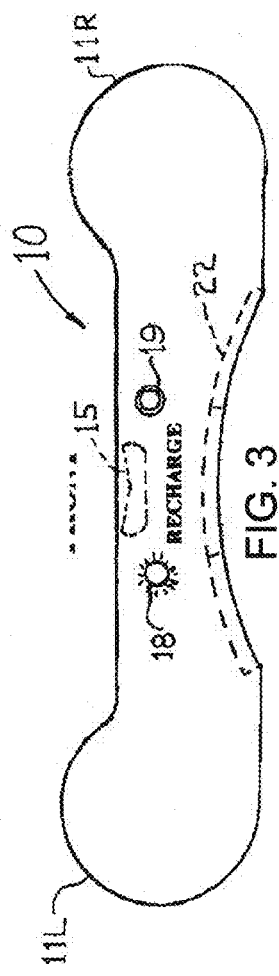
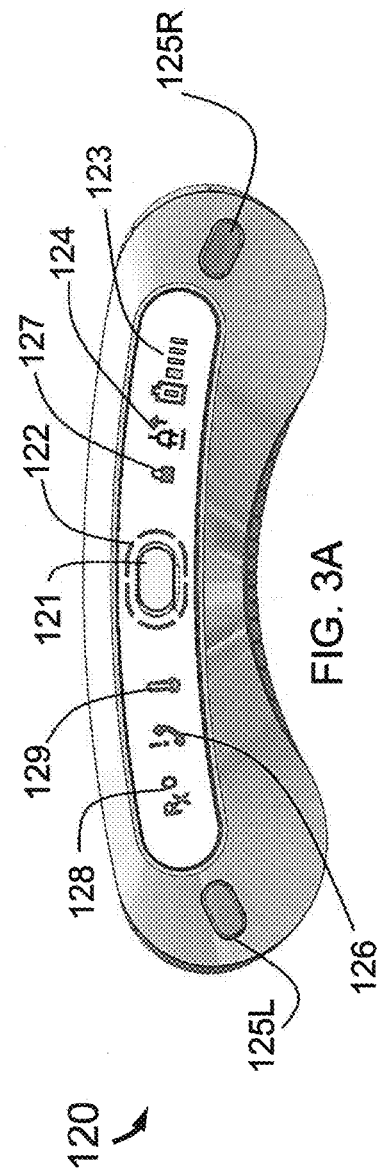
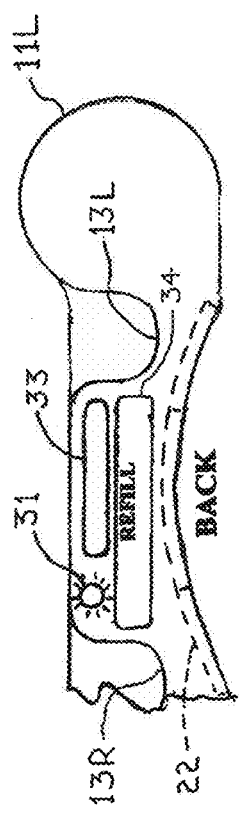

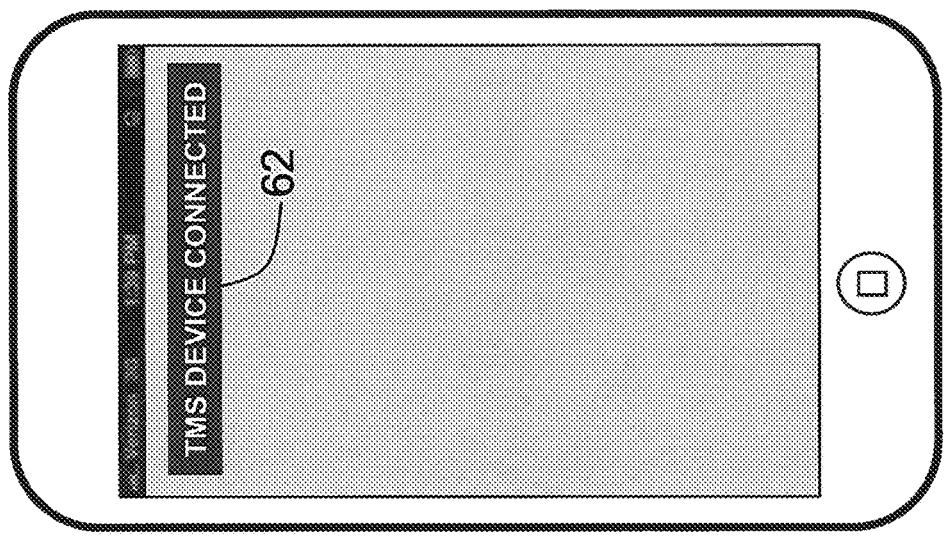
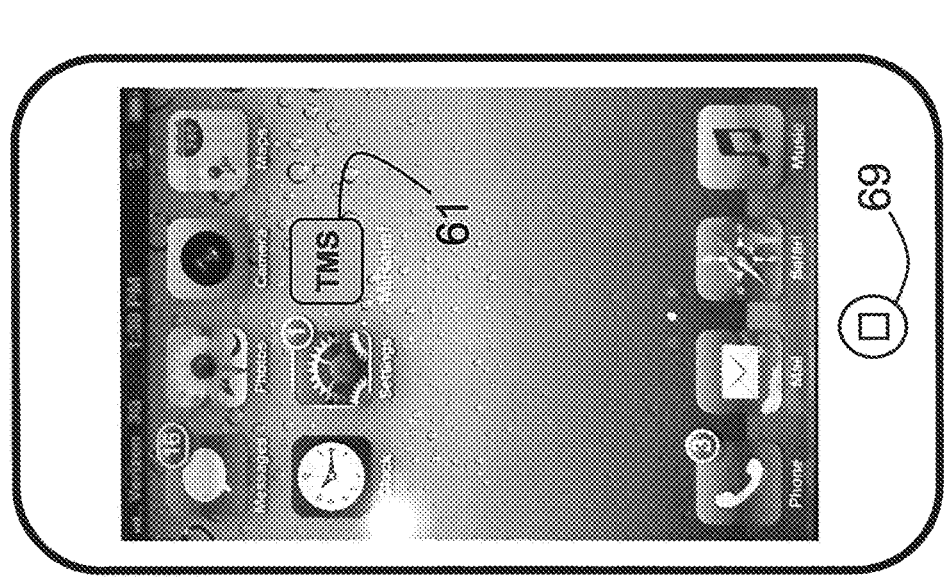
FIG. 7B
FIG. 7A

TRANSCRANIAL MAGNETIC STIMULATION DEVICE FOR THE TREATMENT OF MIGRAINE HEADACHES

RELATED APPLICATIONS

This application is a Continuation patent application of application Ser. No. 15/346,148, filed on 8 Nov. 2016, which is a Continuation-in-Part of application Ser. No. 14/275,927, filed on 13 May 2014, now pending. The entire disclosure of the prior application Ser. Nos. 14/275,927 and 15/346,148 are considered a part of the disclosure of the accompanying application and are hereby incorporated by reference.

FIELD OF USE

This invention is in the field of methods and devices that use an intense magnetic pulse to treat migraine headaches or other neurological disorders.

BACKGROUND OF THE INVENTION

Migraine headaches occur in approximately 12% of the world population. Therefore, in the United States in the year 2013 there were approximately 36 million people who suffer from this affliction. Although medicines have been created that significantly diminish the suffering of migraine patients, these medicines are often contraindicated and have highly undesirable side effects and many patients do not obtain satisfactory relief from the severe headache pain, nausea and other discomforts associated with migraine. Furthermore, migraine headaches are typically treated after they have become painful, i.e., the treatment is often ineffective in preventing the onset of the migraine headache. A non-invasive, non-drug method for the treatment of migraine headaches would be a remarkable boon for those millions of people all over the world who suffer from these painful and often debilitating experiences.

In 1985, A. T. Barker, et al (*Lancet*, 1985, pp. 1105-1107) described the use of a coil placed over the scalp which produced a high intensity, time varying, magnetic field. This time varying magnetic field induces an electric current in the cortex of the human brain which can in turn produce certain effects on the activity of brain neurons. This type of system has been given the name Transcranial Magnetic Stimulation (TMS). If continuously repetitive magnetic pulses are applied in this manner, it has been given the name rTMS. If a single pulse is applied, it has been given the name sTMS. If a treatment includes many pulses, but the pulses are not continuous, even though there are several pulses, this treatment is still called a treatment with a multiplicity of sTMS pulses.

In an article from *Advances in Therapy*, May/June 2001 and entitled "Impulse Magnetic-Field Therapy for Migraine and Other Headaches: A Double-Blind, Placebo-Controlled Study," by R. B. Pelka, et al, there is described a device using an alternating magnetic field source placed on a ribbon around the patient's neck. All devices were no more than 12 inches from the patient's head. The intensity of the 16 Hz magnetic field at the source was 5 microTesla. For all patients, the field at the brain had to be less than 1.0 microTesla. This field was applied for 4 weeks with some benefit being reported in 1 to 3 weeks. The wearing of such a device for weeks is certainly inconvenient as compared to a single magnetic pulse applied for a fraction of a millisecond or at most, a few such pulses. It is also believed that a magnetic field strength of only 1 microTesla would be totally insufficient to erase the aura that precedes many migraine headaches or to be effective to relieve the headache itself.

In the journal *Neurology* (Apr. 11, 2000, pp. 1529-1531) it has been reported by B. Boroojerdi, et al that rTMS at a rate of one pulse per second can create a reduction of the excitability of the neurons of the human visual cortex. However, that article did not indicate that TMS or rTMS can be used for preventing the occurrence of migraine headaches or diminishing the intensity or duration of a migraine headache.

In U.S. Pat. No. 6,402,678, Robert E. Fischell et al describe means and methods for the treatment of migraine headaches using a portable device that is placed onto the patient's head. This device is used to create a magnetic pulse that acts upon the neurons of the brain and can eliminate both the aura that occurs prior to a migraine headache and a migraine headache after it has started. However, since the entire device is placed onto the patient's head, it is somewhat awkward for the patient's use. Furthermore, since the triggering controls are also located on the head mounted device, their operation is also somewhat difficult.

In U.S. Pat. No. 8,262,556, Robert E. Fischell et al describe a TMS device that has an insertable USB KEY to provide the device the ability to provide a prescribed set of additional pulses with the device having a pulse counter that limits the allowable total number of pulses that can be delivered before an additional prescription USB key is required. This method does not allow for a pre-specified prescription time period for example, a doctor might desire to have the prescription allow a large number of pulses but only for 3, 6 or 12 months before they would like to review the patient's treatment.

While U.S. Pat. No. 8,262,556 discloses the ability of the TMS device to monitor magnetic pulse strength and provide an error message if it is not within a specified range, it does not disclose a wide range of other important error conditions that should be monitored in a patient operated portable TMS device for the treatment of Migraine headaches.

A device called the "Spring TMS" device has been created by a company called eNeura, Inc. and has been used by many patients for the treatment of migraine headaches. Although this device has been very successful for this treatment, it also has several disadvantages. A first disadvantage is that it is quite large and weighs about 4.0 pounds, which makes it somewhat awkward to be carried in a women's shoulder bag or handbag. Still further, it has two movable handles each having two recessed slide operated switches to operate the device and trigger the treatment delivery. The moveable handles complicate the placement of wires that must extend to the slide switches in those two handles for initiating the magnetic pulse. Furthermore, frequent bending of these handles in order to operate the TMS device has the potential to cause wire breakage. Another less than optimum feature of the Spring TMS device is a copper coil having an elliptical shape that is non-optimum for the creation of the desired magnetic pulse from a point of view of its efficiency of converting drive current into magnetic field strength and its weight. The copper coil has a spherical curvature with a radius of 4.5 inches (11.4 cm). The radius of curvature at the top of many human heads appears measure at about 10 cm. Therefore, having a coil to create the magnetic pulse that has a radius of curvature of approximately 10 cm would be much better suited to concentrate the maximum magnetic pulse intensity into the patient's brain. Furthermore, the use of an aluminum coil has the desirable attribute of being lighter in weight as compared to a copper coil that can create the same intensity of magnetic pulse.

Instructions to operate the Spring TMS device are provided by audio cues and further by graphic icons and text messages displayed on an LCD display on the top surface of the device. The language displayed on the LCD is English. For sales in countries other than those countries where English is the native language, the Spring TMS software must be programmed to provide a language other than English. A maximum of three languages is allowed for the Spring TMS device therefore requiring different firmware for languages beyond the first three. Since there are many countries with large populations of patients having migraine headaches such as Japan, China, India, etc., and particularly in countries that do not use the Roman alphabet, it would be more cost effective to not require support for the language of every country where the device will be used for the treatment of migraine headaches.

The Spring TMS device also uses off the shelf resistors to bleed of any residual energy left in the coil following delivery of a magnetic pulse. The construction of these resistors provides a potential point of life limiting failure for the device as the resistance wires that form the resistor are welded into an end cap that with the huge magnetic pulses causing forces on the wires can break over time.

The Spring TMS device has separate power and charge buttons and stays on for around a minute after a pulse is delivered to allow a follow on pulse to be initiated if more than one pulse is being delivered in a session. Use of 2 buttons makes the device more complex and leaving the power on for longer reduces overall battery life.

Spring TMS also uses a single microcontroller that both interfaces with the user controls and display as well as the charge/discharge circuitry. Using a single microcontroller means the control lines are longer and are more susceptible to noise. The new device with two processors allows control lines to be shorter and oriented optimally on each board to achieve less susceptibility to noise.

Spring TMS has a single cylindrical curve on the surface that is applied to the patient's head that does not help in establishing the correct position up or down for the device with respect to the area of the brain to be treated.

In US patent application (Ser. No. 14/275,927) Fischell et al describe the use of encapsulation or potting to reduce the movement of the magnetic coil including its end wires to reduce the noise level during a pulse and improve device reliability. What is not disclosed are designs that improve the device reliability of other components in the TMS device that are also exposed to the forces generated by the large magnetic pulses.

The current SpringTMS device provides no security capability to ensure that only the prescribed patient can use the device. The SIM card is matched to the device but it can still be borrowed by another person and used.

The current SpringTMS device uses a single charging circuit for its two capacitors and uses only two circuit boards with no special orientation. The large magnetic pulses generated by a TMS device will induce significant forces on individual wires and electrical components that can over time and thousands of pulses result in mechanical failures unless novel design techniques are applied to these wires and components.

SUMMARY OF THE INVENTION

The present invention is a means and method for improving the treatment of any number of disorders of the brain that can be treated by creating electric currents in the brain by the application of a high intensity, short duration magnetic pulse or a series of such pulses. An example of such diseases includes all types of headaches, depression, obsessive-compulsive disorder, insomnia, bipolar disease, epileptic or febrile seizures and status epilepticus. It is also anticipated that an intense, short duration, magnetic pulse or a collection of pulses could be applied as therapy by stimulation of a variety of nerves such as the occipital nerve or the trigeminal nerve in the region of the head and the vagal nerve in the region of the neck. It is also anticipated that magnetic pulses applied to the carotid sinus and/or vagal nerve in the neck can be used to stop an episode of cardiac arrhythmia such as atrial fibrillation. This invention also envisions the use of the magnetic pulse(s) to prevent the occurrence of such brain and nervous system disorders rather than to merely treat them when they have occurred. As such, periodic use (for example daily use) of magnetic pulses may be beneficial in improving sleep and reducing the incidence of neurological disorders of the brain such as epileptic seizures and migraine headaches. The method of use of the TMS device includes such periodic use and/or responsive stimulation use to relieve primary symptoms and/or prodromes or auras that occur before the primary symptoms of a neurological disorder of the brain.

For the purposes of this disclosure, the present invention envisions the use of a single TMS pulse or several single TMS pulses. An important use being the treatment of migraine headache as will be described herein in detail. However, it should be understood that the system used for the treatment of migraine headache could also be used for the treatment of other disorders such as those mentioned herein. It should also be understood that a multiplicity of single magnetic pulses could be used instead of only one pulse. These multiple pulses could either be a multiplicity of single pulses that are spaced apart by several seconds to several minutes, or they could be rTMS which is a continuous train of magnetic pulses. Although the patient will be described in this specification as being of the female gender, it should be understood that the invention can be used by either males or females and by children or adults.

The present invention is a single unit, portable magnetic TMS device that can be placed by the patient onto any region that is near or touching her head or any other appropriate place of a human being. This TMS (Transcranial Magnetic Stimulation) device can be powered by a primary battery, a secondary rechargeable battery, from an AC mains receptacle through an AC to DC converter or DC from an airplane's or automobile's commercial power-accessory receptacle. After the device is turned on, a charge switch can be pressed by the patient to begin charging the capacitors to a comparatively high voltage. While charging occurs, a visual display would clearly indicate that the capacitors are charging. Ideally, a circular display consisting of several light-emitting diode (LED) indicators would turn on sequentially indicating the progression of the charging cycle. Alternatively, it is conceived that the TMS device could employ a linear bar that progressively fills over time as the capacitors are charged. If for example, only 4 or 5 LEDs are used, then each sequential LED could begin in the off state, then flash and then go solid on. If a multicolor LED array is used, the LEDs could begin in the off state, turn amber and then green. The sequence of LEDs indicating that the capacitors are being charged might ideally have an amber color as an indication of attention, that the capacitors are accumulating the energy needed to create the electrical current pulse in the magnetic coil. When the capacitors are fully charged, a visual indicator, such as an illuminated green LED, would show that the capacitors have accumulated the necessary energy and are ready to be discharged into a low electrical resistance coil, causing an electrical current to flow, to produce a high intensity, short duration, magnetic pulse. It is highly desirable that the visual display that is used would be of a color intuitively associated with proceeding with the treatment, such as a green light that is used in traffic to indicate "go ahead."

A preferred embodiment of the system would have a single button that both turns on the device and initiates a charging cycle. After a pulse is delivered, the present invention with a single button would remain on for a period of less than 15 seconds during which re-pressing the single button will initiate another charge cycle. If not re-pressed, the device would turn off to save battery life. This differs from the Spring TMS device with 2 buttons and a much longer time-out period.

It is also envisioned that there could be an additional pre-set time limit during which the patient must deliver the pulse by placing the TMS device in the proper position and depressing one or more buttons on the surface of the device. If that time is exceeded the device would discharge the capacitors and turn off so that one can not leave a live charge device around where it could be accidentally discharged.

If the patient fails to delivery the pulse in the pre-set time, a bleed out resistor will automatically discharge the capacitors safely and the device will turn off. If a pulse is delivered, the single button can be depressed again to initiate an additional pulse if desired. If no additional pulse is desired, the device will turn itself off after a set time.

To prevent accidental charging of the capacitors, the charge switch could be under a cover, be a slide or rotary switch, could be recessed below its immediately surrounding surface on the top surface of the TMS device, require activation for a fixed period of time or any other technique that provides a means to prevent inadvertent charging. If the TMS device has an ON-OFF switch that is recessed, and is a type that is difficult to inadvertently turn on such as a rocker switch, then inadvertent charging could virtually never occur since it cannot occur before the ON-OFF switch is turned to the ON position and then, the capacitor charge switch is later activated to charge the capacitors. Similarly, if the TMS device has a combined CHARGE-ON-OFF switch that has stable ON and OFF positions but a momentary (i.e. spring-returned) CHARGE position then inadvertent charging could virtually never occur since it cannot occur before the ON-OFF switch is moved from the OFF position to the ON position and then later, past the ON position and momentarily to the CHARGE position to activate the charging of the capacitors. Such a three-position switch would preferably be a recessed slide or rocker type. Because it will be valuable for female patients to be able to place their TMS device into their handbags, it is quite important to prevent inadvertent operation of the TMS device when so placed. By having a recessed ON-OFF switch of the slide or rocker design and having a recessed CHARGE switch or a combined-function CHARGE-ON-OFF switch, inadvertent charging of the capacitors would be virtually impossible.

A recently designed TMS device called the "Spring TMS" (Total Migraine System) device received CE Mark for sale in Europe in 2011 and was approved by the US FDA in 2014. This device has been used successfully by patients to prevent and acutely treat migraine headaches. However, some problems with that device are its weight, of 3.7 pounds, a size somewhat too large to be placed into a handbag, and moveable handles that include a switch to trigger the magnetic pulse. Requiring wires to pass through a moveable handle to operate the magnetic pulse could also result in some lack of reliability for the Spring TMS device. The present invention is a significant advance by having the two capacitors surrounded by a plastic cover that forms a handle for each hand that can be held by the patient's hands in such a way that the patient's thumb and fingers actually wrap around the cover that surrounds the capacitors. This is a very comfortable way for securely holding the TMS device for easy and accurate placement onto the patient's head and for holding the device in place on the patient's head while waiting for the magnetic pulse to occur.

It is also envisioned that custom capacitors could be formed in the shape of a portion of the device case, reducing the size further.

By not having two handles with two switches to operate the TMS device, inadvertent wire breakage is eliminated and the device's weight and size are somewhat reduced. Still further, the treatment of the patient's migraine headache is further improved by having the magnetic pulse occur automatically at a set time after the green LED light has indicated that the patient should place the device on her head. For example, after the green LED is illuminated and a pleasant sound is created by the TMS device, the patient would have between 4 and 12 seconds to position the TMS device on her head or other place on her body that is the optimum location for her treatment, prior to the delivery of the treatment TMS pulse. An optimum time for such placement would be $7\pm1$ second after the LED light turns on. After this time period the treatment would be automatically delivered. This novel concept has several important advantages. The first is that it will not be necessary for the patient to actuate a switch when she wants the pulse to occur. Another advantage is that there will not be a need for another switch on the surface of the TMS device to trigger the magnetic pulse. A third advantage is that if, by some totally unexpected event the capacitors become inadvertently charged, they will be automatically discharged in about 7 seconds so that there will be no damage to the capacitors by remaining charged for a long period of time. It is also understood that a pressure or proximity switch could be included that only allows discharge through the coil if the device is touching the head. If not in close proximity to the head, the device could be designed to discharge the capacitors through a resistor instead of through the magnetic coil.

In another embodiment, once the capacitors are fully charged, the TMS device could begin a countdown such as the self-timers on cameras where a LED or light would flash slowly at first then faster then go solid on, and then the pulse would be delivered. A soft tone or a clicking sound that would not aggravate the patient's headache could be used by itself or with the LED light with the same pattern of speeding up, then going steady on just before the pulse is delivered. In this way, once the pattern begins, the patient need only place the TMS device in the appropriate place on the head and wait until the pattern stops and then the pulse would be delivered.

The high intensity, short duration, magnetic pulse would, by Faraday's Law, induce electric currents in the neurons of the brain (or elsewhere in the body) that would be a treatment for the patient's disorder. For example, if the magnetic pulse was applied to the occipital lobe of the brain during the visual aura before a migraine headache, the aura could be substantially erased and the patient would not progress to having a migraine headache. The magnetic pulse applied to another region of the body could be used to generate an electric current pulse at that location, which electric current pulse could be therapeutic.

An important factor in the design of the TMS device is its ability to limit the number of pulses that the patient could apply to her brain without authorization from the physician who prescribed the device for the patient's use. If there were an unlimited number of pulses that the device could deliver, a patient might inappropriately allow an unauthorized person to use the device without a proper prescription from a doctor. By limiting the number of pulses that could be applied without a refill prescription from the patient's doctor and by charging a moderate amount of money for each pulse that is used, the patient will not be tempted to allow others to use her TMS device without a proper prescription from a licensed physician. It should however be understood that a device which can apply an unrestricted number of pulses is conceived of as included in the concept of the present invention.

A potential safety aspect of this invention is that the TMS device could limit the number of pulses per unit time that the patient could receive. For example, the device could be designed to disallow more than (let us say) ten pulses in any one-hour period.

Because doctors may believe that the patient should be seen periodically, it is also envisioned that the prescription that is provided by an insertable SIM card or flash memory card should have a time limitation in addition to or instead of a pulse limitation. For example, the doctor might provide a 3, 6, 12 or 24 month prescription without a limit on pulses or with a secondary limit of pulses.

To satisfy the need for a refill of available pulses and reading data into and out of the TMS device, it could include a wired data communication interface (physical connection port and associated data communication protocol) such as any standard computer input-output connection including, but not limited to, RS-232, USB, Ethernet LAN, IEEE 1394 (FireWire®), Lightening®, etc. to connect to a computer which has access to a central server via the Internet. An alternative wired data communication interface could be a custom-engineered connection port with a supporting communication protocol and interface circuitry. An alternative wired data communication interface could use the standard RJ-11 telephone jack supported with a modulator-demodulator (modem) circuit and a communication protocol to communicate digital information over standard land-line telephone voice network to a central server. With such a wired data communication interface as generally described above, the patient could allow the device manufacturer, who controls access to the central server, to add pulses over a connection as allowed by a refill prescription from the patient's doctor. Also, this connection could be used to transmit date and time stamped pulse usage data from the TMS device to the patient's doctor or a central diagnostic center for patient monitoring. The connection could also provide device diagnostics including appropriate information if the TMS device was not operating properly. An alternative means for providing additional pulses and reading data into and out of the TMS device would be by means of a wired USB connection or any other standard type of computer input data communication connection to a personal computer. When a connection is made between the TMS device and a computer, the USB interface could be used to convey an increase in the number of allowed pulses. Of course, any refill of pulses would have to be authorized by a valid and current refill prescription from the patient's doctor or any other authorized medical practitioner.

The USB interface could connect a USB key such as a standard USB thumb drive containing encoded data that will instruct the TMS device to allow a prescribed number of allowed pulses over a predetermined period of time. In any case, the TMS device would be designed so that the USB key would only enable additional pulses one time. Removing and reinserting the USB key a second time would not add additional pulses. In addition, other standard flash memory devices such as a compact flash card, SIM card, memory stick or SD card could be used instead of the USB thumb drive or USB key to add additional pulses for the TMS device.

It is envisioned that other telecommunications interfaces such as wireless data communication could be used instead of a wired connection to reach the central server through the Internet. Wireless data communication interfaces include, but are not limited to, 3G/4G cell phone network, IEEE 802.11 (WiFi), IEEE 802.15.1 (Bluetooth), etc. A TMS device incorporating a 3G/4G compatible wireless interface would connect to the central server directly through the wide area network (WAN) commercial cell phone system using a digital data plan. Such a TMS device would be capable of receiving a prescription refill at any time or geographic location with cellular telephone coverage. A TMS device incorporating an IEEE 802.11 (WiFi) wireless interface would connect to a local WiFi router or WiFi hot-spot that is, in-turn, connected to the Internet by a wired or other wireless data communication medium. The WiFi compatible TMS device would connect to the central server and thus also be capable of receiving a prescription refill and exchanging information with the central server. A TMS device incorporating an IEEE 802.15.1 (Bluetooth) wireless interface would connect to a local, near-by, device such as a smartphone, personal computer, tablet, etc. that is similarly-equipped with a Bluetooth personal area network (PAN) interface.

A preferred embodiment of the present invention would use a standardized Bluetooth wireless connection between the TMS device and a device such as a smartphone, tablet or PC that is connected to the Internet. An APP or program on the smartphone, tablet or PC would enable both the delivery of new prescription pulses to the TMS device as well as device history and diagnostics to the provider of the TMS device and the patient's physician. Of course any refill of pulses, affected by these wireless communication means, would have to be authorized by a valid and current refill prescription from the patient's doctor or another qualified and authorized medical practitioner.

Because (using one mode of the present invention) there would be a limited number of pulses available to the patient, it would be important for the patient to know the exact number of pulses remaining. To that end, an LCD, LED (or other) display (or audio) could be provided that indicates the number of pulses remaining. If the number of available pulses dropped to that number that would be used by the patient in only a few days, the patient could ask the doctor for a refill prescription or the refill prescription could be on file with the organization that provides a variety of patient services. The patient could then receive a refill from the patient services organization through the telephone connection or by means of the USB key or over the Internet from the central server. It should be understood that once a patient has a previously used USB key, a refill could be accomplished by the use of the USB slot in a personal computer that is connected over the Internet to the TMS device manufacturer (or an authorized service organization) who could verify the refill prescription and the source for payment for the pulses and send the properly encoded data to the USB key to permit additional pulses. The patient would then remove the updated USB Key and insert it into the TMS device to add the prescribed number of pulses and time duration during which time the device would function.

It is also understood that the USB key could be sent by mail or purchased at the patient's local pharmacy. It should also be understood that a date and time stamped history of the number of pulses used could be made available to the doctor or the manufacturer by means of the telephone connection or the USB interface from data stored in a digital memory in the TMS device. The USB interface would work by either connecting using a cable to a personal computer or by transferring the data to the USB key which is then inserted in a the USB slot of a computer connected to the Internet.

As disclosed in U.S. Pat. No. 8,262,556 by Fischell et al, it should be further understood that the TMS device system could include a self-checking means that would verify that the magnetic pulse was within a specified limit of amplitude and time duration. This could be accomplished by a separate wire coil located near the device's magnetic coil that would measure the amplitude and time course of the magnetic pulse. Another means to verify magnetic field pulse characteristics is to use a semiconductor sensor, such as a Hall effect sensor, with correct position and orientation to detect the magnetic field produced by the pulse. If either the amplitude or time course of the magnetic pulse were out of their specified limits, the magnetic TMS device system could produce an error signal that would be detected by the patient and could also be determined by a patient's service center via a telephone or Internet connection. The warning could be by means of a visual display or by means of a voice warning.

It is also highly desirable to have a number of additional checks provided by the control system for the TMS device to ensure that both the charging and discharging cycles are with specifications. These include error monitoring of each of the following with an appropriate error message if the: 1) peak voltage for each capacitor is too high or low, 2) the charge rate for each capacitor is too high or low, 3) the discharge rate if there is a timeout for each capacitor if no pulse is delivered is too high or low or 4) the voltage difference between caps is too high or low.

Additionally, the patient could be provided with a separate device that could be used to check the amplitude and time course of the magnetic pulse. This could be an external device onto which the patient places the TMS device, then actuates the TMS device and then the external device measures the magnetic pulse. It is also envisioned that a closed-loop control system could be used where the level measured on the previous pulse could be used to change the charge parameters on subsequent pulses to maintain the magnetic pulse within pre-defined limits. Such calibration could be manual (such as a "calibrate" button) or automatic, done each time the TMS device pulses.

Also as disclosed in U.S. Pat. No. 8,262,556 another important aspect of the invention is that each TMS device would have a unique serial number that is recorded for a particular patient. When the TMS device transmits the stored data on pulse usage or receives instructions to add pulses, the data transmitted to and from the TMS device must be encrypted so that it would be essentially impossible for an unauthorized person to add pulses to the TMS device or to gain access to the patient's use of pulses to treat her brain (or other) disorder. Furthermore, a secure link could allow the patient to be recognized only by her serial number so that her actual name would not be known to the operator at the manufacturer's service center. Thus patient confidentiality would be maintained. An optimum serial number for a patient could be that patient's three initials followed by a number that would be the greatest number of patients that would ever be expected to have those three initials. For example, the first patient having the initials AAA would also have the numbers 00001 added after those initials so that her serial number would be AAA00001. This type of serial number would therefore accommodate one hundred thousand patients all having those same three initials. If the patient would have more than three names, then the three initials to be used would be the first letter of the first, second and last name. For hyphenated last names, the first letter of the first name and each of the two letters of the hyphenated name would be used. If the patient had only two names, then the initials of the first and last name would be used with the letter "N" placed in between.

This type of serial numbers would be used only for patients in a country that uses the Roman alphabet and numbers as used in the United State of America, North and South America, the majority of the countries of the European Union, New Zealand and Australia. For patients in any other country that does not use that alphabet, an eight digit serial number consisting entirely of numbers would be used. Of course having eight numbers would allow essentially one billion patients to have a different serial number.

The present invention would also include the matching of the SIM card or USB key to a specific TMS device that would preclude a patient loaning a SIM card with non-expired pulses to another patient for use in their device. An additional security measure is also envisioned on having the activation button include a fingerprint sensor such as found on the Apple IPHONE 6 smartphone. Thus only the patient could activate their device. An even more stringent security measure would have the fingerprint reader in the pulse activation button or in a special spot where the patient would place one or more fingers that are not pressing the activation button but are used to hold the device. Thus a patient could not activate their device and allow another person to easily use it.

In studies using the Spring TMS device, daily use in the morning and evening of 2 to 10 pulses in addition to acute treatment at the start and during the progression of a migraine headache has shown to be effective. This means that over a 5 year period, the device might need to delivery many thousands of pulses. This requires a device that his highly reliable, which is a difficulty in a device delivering thousands of amperes of current to produce a very strong magnetic pulse. A number of novel aspects of the present invention are disclosed here that greatly improve the reliability of the TMS device.

Another important aspect of the present invention is the shape and material of the magnetic coil. In U.S. Pat. No. 5,116,304, J. A. Cadwell describes a magnetic coil that has the shape of a skullcap. Cadwell states that this coil can be made from "Litz wire or copper strip wire" but he never envisages aluminum wire with a rectangular cross section which is optimum for a TMS device because of its low electrical resistance with significantly reduced weight. Also, the cost of aluminum wire is distinctly less than the cost of Litz wire whether the Litz is formed from copper or aluminum. The optimum shape for the aluminum wire coil is in the shape of a spherical sector that somewhat matches the spherical curvature of the head. Measurements have indicated that the radius of the spherical sector should be approximately 10±1 cm. The optimum arrangement of the aluminum wire having a rectangular cross section is to have the long extent of the rectangular wire being situated generally vertically outward from the patient's head.

Another important aspect of the present invention is the shape and orientation of wires and components on the coil and printed circuit boards within the device. The compact geometry of the device requires that the control electronics be located near the TMS coil and that these electronics function reliably within a high magnetic field environment. The high intensity electromagnetic pulse generated by the TMS coil induces an electric current pulse in the surrounding conductive parts that are cut by the magnetic field lines. The current pulse induced in each of these conductive parts generates localized opposing electromagnetic fields. The opposing fields generate repelling forces among the TMS coil and the surrounding conductive parts.

Because of the high magnetic field amplitude, these repelling forces applied to any individual wire or electrical component can over time and thousands of pulses result in dislodgement of the wire or component.

The highest repelling force and induced current occurs in the two shapes of the conductive components:
 a. Any conductive plate exposed to the time varying magnetic pulse flux lines experiences an induced electric current. This current is typically referred to as an eddy current. The magnitude of the current circulating in the plate is maximum when the plane of the plate is perpendicular to and cut-by the flux lines. The induced eddy currents will generate an opposing electromagnetic field pulse. An opposing mechanical force results. The conductive plates in the device are, for example, the copper plane layers in the PCB boards, heat sinks incorporated into the body of some high power components, and any conductors with large cross-sectional ratios of width to thickness.
 b. Any wound or looped conductive wires exposed to the time varying magnetic pulse flux lines experiences an induced current. The magnitude of the induced current is maximum when the plane of the loops are perpendicular to and cut-by the flux lines. The induced current will generate an opposing electromagnetic field pulse resulting in an opposing mechanical force. The wound components present in the device are, for example, electrical transformers, inductors, and wound power resistors.

Because of the large magnetic fields, the forces applied to any individual wire or electrical component can over time and thousands of pulses result in dislodgement of the wire or component. These include:
 1. Orientation of the inside end wire in the could aligned with the magnetic field disclosed in US Patent application (Potting 3GCIP)
 2. Orientation and geometrical placement of the printed circuit boards
 3. Orientation and placement of the individual components on the printed circuit boards
 4. Attachment by wires or ribbon cables of one printed circuit board to another.
 5. Use of flex jumpers between printed circuit boards
 6. Use of additional encapsulation or adhesives to immobilize wires or components that might otherwise move in response to the forces induced by the magnetic pulse.
 7. Use of a single rigid flex printed circuit board that can be folded into the final three dimensional shape.
 8. Use of a single three dimensional printed integrated printed circuit board forming two or more sides of an open box. This could be done by 3D printing technology.
 9. Development of a custom bleed resistor that can reliably tolerate thousands of large magnetic pulses without internal breakage.

As disclosed in US patent application (Ser. No. 14/275,927) by Fischell et al, another feature of the present invention is to "pot" (i. e., encapsulate) the coil by encapsulating it in a plastic material. This will reduce the noise produced when the pulse is delivered as well as reduce unwanted mechanical stress on the coil wires, which will improve the longevity of the coil. In addition to reducing the acoustic pulse of the energized TMS coil, potting also provides high-voltage electrical insulation to reduce electrical breakdown between and around the high voltage circuit elements. There are several different embodiments of "potting" to reduce noise and increase the life of the coil including:
 1. Stabilization or immobilization of the end segments of the coil that attach to an end connector which attaches to the high voltage circuit board. If left mechanically unsupported or cantilevered, the end segment can become dislodged from the end connector or cause the end connector to become dislodged from the high voltage circuit board as a result of the magnetomotive forces generated by the delivery of the magnetic pulse. Such stress leads to mechanical degradation and failure and corresponding electrical failure. The maximum stabilization or immobilization of the end segments of the coil is achieved by minimizing the mechanical bending deflection of the length of the end segments. This length is defined as the distance of the end segment between the point where it separates from the coil body and the point where it terminates electrically. For a simple beam of uniform cross section with moment of inertia I, modulus of elasticity E, length L, with an applied transverse load W, the deflection y at any point x along L is given by the standard formula:

$$y=W*x*(L-x)*[L^2+x*(L-x)]/(24*E*I*L).$$

The greatest deflection occurs at position x=L/2, midspan. For this point the deflection simplifies to:

$$y=(5/384)*(W*(L^3))/(E*I).$$

Thus for a given end segment constructed with given materials and shape properties (which define its moment of inertia I, modulus of elasticity E), the deflection for a given load is proportional to length cubed. The least deflection is achieved with the shortest length end segment. Ideally, the length of an unsupported end segment may preferably be 1 to 5 times, the thickness of the end segment wire in the direction of the magnetomotive force. Under no condition should the length of an end segment even if supported be more than 20 times, the cross section thickness of the segment in the direction of the magnetomotive force. For example if the could wire has a dimension of 0.30 inches in the direction of the magnetomotive force, then the ideal length should be less than 1.5 inches (5×) and under no condition should it exceed 6 inches (20×).
 2. Stabilization or immobilization of the end segments of the coil that attach to an end connector which attaches to the high voltage circuit board by means of a shaped electrically-insulated material. One such a shape includes, but is not limited to, a wedge that conforms to both the curvature of the coil and the end segment. This element allows gradual separation of the coil's end segment from the coil body while providing mechanical support along the majority of the end segment's length. Another such shape includes an ovoid shape that mechanically mates with the coil and end segments, thus immobilizing the end segments with respect to the coil's body. Yet another such shape includes electrically-insulated sleeving that both supports the end segment and prevents frictional contact with the coil's body. Such frictional contact may degrade the electrical insulating properties of the coil's windings thus leading to electrical failure.

3. Encapsulation of the entire coil including the end segments in a solid material, for example a plastic.

In addition to potting, another improvement in design of the coils that is part of the present invention is routing of the coil's end segments, as they progress away from the coil's body, in such a direction that the mechanical deflection due to the magnetomotive force generated by the delivery of the magnetic pulse is minimized. The preferred routing direction is parallel to the magnetic field produced by the coil proper. The position of the end segment's separation from the coil depends on the coil's geometry and the electrical properties one it trying to achieve with a given coil design.

As disclosed in US patent application (Ser. No. 14/275, 927) by Fischell et al, in addition to potting, another improvement in design of the coils that is part of the present invention is winding the coil with rectangular, rather than round cross-section conductors including both Litz wire and solid ribbon wire. Round cross-section conductors, commonly in use and easily available, result in lower wound-coil packing factors than the use of rectangular cross-section conductors due to the air or potting voids between the round conductors. Rectangular conductors provide increased bonding of winding layers, turn-to-turn. Use of rectangular conductors result in coils with increased mechanical strength when wound, due to the minimization of voids between winding turns. In addition, coils fabricated from rectangular conductors have a higher ratio of conductor to overall coil cross-section. Such benefits as these result in higher reliability and lowered susceptibility to the mechanical forces created by the high magnetic field sTMS pulse. Still further, such coils (particularly when formed from aluminum) offer a lower weight for the magnetic coil.

In addition to potting and winding the coil with rectangular cross-section conductors, another improvement that is part of the present invention is the coil's connections to the high voltage circuit board with bonding means by welding or soldering that employ high tensile- and shear-strength metal alloys containing very low, less than 0.1% (1000 ppm), or 0% metal lead (Pb). Common electrical connection methods include but are not limited to: gluing with conductive adhesives, soldering with metal alloys (liquidus temperatures typically 350 C or less), mechanical contact compression, spot-welding with high-current, and electric-arc or gas welding/brazing with metal alloys (liquidus temperatures typically 400 C or above). When conducting high currents, much greater than 5 amperes for example, at high voltages, much greater than 50 volts for example, electrical contacts can experience thermal stress which loosens and fatigues the connection due to increased electrical resistance and subsequent temperature rises from I×R heating. Thermal cycling of the contact along with magnetomotive forces may result in mechanical stresses which loosen the contact resulting in undesired intermittent electrical connection. Mechanically-loose, intermittent connections which carry high currents at high voltages may experience the formation of plasma arcs in and around the loose connection points. Such plasma arcs can vaporize the connection's metal materials and connector structures degrading the connection and leading to electro-mechanical failure of the connection. Bonding the coil's connection to the high voltage circuit board by means of welding, brazing or soldering with high tensile- and shear-strength lead free metal alloys relative to 63/37 (63% Sn-37% Pb) solder, for example: 95% Sn-5% Ag, or 97.5% Sn-3.5% Ag, can improve connection strength and reliability.

Another embodiment of the present invention would use two or more coils each taking the discharge from its own high voltage capacitor to achieve the same level of magnetic field in a smaller device.

An important feature of the TMS device is a first audio signal means to indicate to the patient that the capacitors have been fully charged and the patient should place the device on her head. A second audio signal that will indicate to the patient that the magnetic pulse has occurred. Ideally, each of these pulses will occur for a time period between 1 and 2,000 milliseconds. Ideally these pulses would be different from each other so that they will be associated with two different events. It should be understood that these pulses could be a single tone or multiple tones or even a collection of musical notes. It should be understood that these sounds could be pre-recorded audio clips, selected from a catalog of such sounds and downloaded into the device through the data communication interfaces previously described. For example the favorite or sentimental ring tones on your cell phone could personalize it for any patient. It should also be understood that the audio signal could be a voice that has an announcement that the capacitors are charged or the statement, "place the device on your head," and the statement, "the pulse has been delivered," could occur after that event has occurred. The language used for the vocal announcements would ideally be in the language of the country where the device was prescribed.

Thus one object of the present invention is to have a magnetic TMS device that is portable and operated by the patient for the treatment of disorders of the brain, the TMS device being designed to provide one or more, high intensity, short duration, magnetic pulses that are applied to the neurons of the brain or to any other body part that is to be treated, the purpose of the treatment being to prevent the pain, photophobia, phonophobia and/or nausea associated with a migraine headache or any other disorder that can be prevented or ameliorated by the use of sTMS (which is the same as TMS) or rTMS. The TMS device having a receptacle for an insertable SIM card containing the patient prescription, the prescription having an expiration date.

Another object of this invention is to have internal components and circuit boards placed in positions to better tolerate the forces applied by a multiplicity of magnetic pulses that can result in mechanical failure. These include: 1) orientation of individual circuit boards, 2) orientation of components on a circuit board, 3) orientation and structure of connectors between individual circuit boards, or 4) encapsulation of use of adhesives to immobilize wires and components other than the magnetic coil Still another object of this invention is to have dual microcontrollers with one connecting to the user interface and the second controlling the charge and discharge of the capacitors through the magnetic coil.

Still another object of this invention is to have a separate charging circuit for each capacitor.

Still another object of this invention is to monitor the operation of the TMS device with error messages provided if the: 1) peak voltage for each capacitor is too high or low, 2) the charge rate for each capacitor is too high or low, 3) the discharge rate if there is a timeout for each capacitor if no pulse is delivered is too high or low or 4) the voltage difference between caps is too high or low.

Still another object of this invention is to have a shaped attachable or integrated ridge element that would help align the curved shape of the TMS device with the back of the patient's head improving proper positioning.

Still another object of this invention is to have a custom bleed resistor formed from a multiplicity of resistance wire coils with the ends of each resistance wire coil directly attached to a circuit board to better immobilize the attachment point and reduce the probability of internal breakage induced by magnetic pulse forces.

Still another object of this invention is to limit the total number of pulses available before a refill takes place and also to limit the number of pulses allowed in a predefined time period.

Still another object of this invention is to have the availability of additional magnetic pulses provided by means of a telephone (or Internet) connection or from a USB key, SIM or memory card from an authorized provider of the pulses and based upon a refill prescription from the patient's doctor.

Still another object of this invention is to have the refill data message in an encrypted format so that a refill of pulses cannot be accomplished without proper authorization.

Still another object of this invention is to have a curved, spherically shaped coil for the TMS device that can create a magnetic pulse over either or both sides of the occipital lobe of the brain, the radius of curvature of the sphere sector being approximately 10±1 cm.

Still another object of this invention is to have a visual display on a TMS device that can show the number of pulses remaining, the status of the capacitor charging cycle and that the capacitors are fully charged.

Still another object is to have a display that indicates the remaining capacity of the internal battery pack.

Still another object of this invention is to have a means to prevent inadvertent activation of the charge switch that starts the capacitor charging cycle.

Still another object of this invention is to have the visual displays be designed as to color (viz. red, amber, green, etc.) and intensity to minimize discomfort for a person experiencing a migraine headache, which patient may be undergoing photophobia, i.e., a high sensitivity to light.

Still another object of this invention is for the TMS device to have an access port for accessing the location of the rechargeable battery so that battery replacement is simplified.

Still another object of this invention is to have a covered access port for a SIM card, which SIM card provides a serial number for the TMS device and the SIM card can also have the capability to set the number of pulses allowed and the time duration allowed for the TMS device to continue to function. This may be set in terms of days, weeks, months or years or may be associated with a specific prescription expiration.

Still another object of this invention is to have a potted coil that will reduce the sound generated by coil wire movement when the pulse is delivered as well as increase the longevity of the coil.

Still another object of this invention is to have an end segment of the coil being immobilized by encapsulating the end portion of the coil that is connected to a terminal.

Still another object of this invention is to have an end segment of the coil being immobilized by an electrically-insulated structure mechanically-mated to the magnetic coil.

Still another object of this invention is to have the magnetic coil fabricated from a metal wire having a rectangular cross-section that provides improved mechanical support, lighter weight and improved reliability with a preferred form for the wire being anodized aluminum.

Still another object of this invention is to have a "self timer" that begins automatically when the capacitors are charged and will activate the pulse after a set time period thereby allowing the patient time to properly place the TMS device onto her head for pulse delivery.

Still another object of this invention is to provide a wireless connection though a smartphone, tablet or personal computer to allow new prescriptions to be downloaded to the TMS device and device diagnostic data and patient use data to be uploaded to the TMS device provider and the patient's physician.

Still another object of this invention is to include a method of treatment that includes use of the TMS device in one or more of the following ways:
 1) Responsive to the aura or prodrome that occurs before the primary symptoms of a neurological disorder;
 2) Responsive to the primary symptoms of a neurological disorder; and/or
 3) Periodic stimulation on a scheduled basis.

Still another object of this invention is to include a method for responsive and/or periodic stimulation of one or more single pulses from a TMS device for the treatment or prevention of one or more of the following:
 1) Migraine headaches;
 2) Epileptic seizures;
 3) Cardiac arrhythmias; or
 4) Sleep disorders.

Still another object of the present invention is to include a method of improving sleep by periodic stimulation one or more single pulses from a TMS device.

The term application program includes APPs that run on a smartphone or tablet as well as a program that runs on a personal computer.

These and other objects and advantages of this invention will become obvious to a person of ordinary skill in this art upon reading the detailed description of this invention including the associated drawings as presented herein.

BRIEF DESCRIPTION OF THE DRAWINGS

FIG. 3 is a front side view of the TMS device showing the LED that indicates the device needs to be recharged and the receptacle for the placement of a power cord to recharge the TMS device.

FIG. 3A is a front side view of a preferred embodiment of the TMS device showing the on/off/charge and activation buttons and the display icons.

FIG. 4 is a partial back side view of the TMS device showing the position of the LED that would indicate that the device should be refilled with magnetic pulses because either the total number of pulses is nearing its maximum allowed number or the time limit has been reached when the TMS device will cease to operate, and also showing the cover over the location where a SIM card would be placed and where the USB connection can be made.

FIG. 7A is a front view of a smartphone showing several APPs including the TMS MiRelief APP.

FIG. 7B shows the wording that would come up on the smart phone after it has successfully completed a wireless connection to the TMS device.

DETAILED DESCRIPTION OF THE INVENTION

Figure 1:
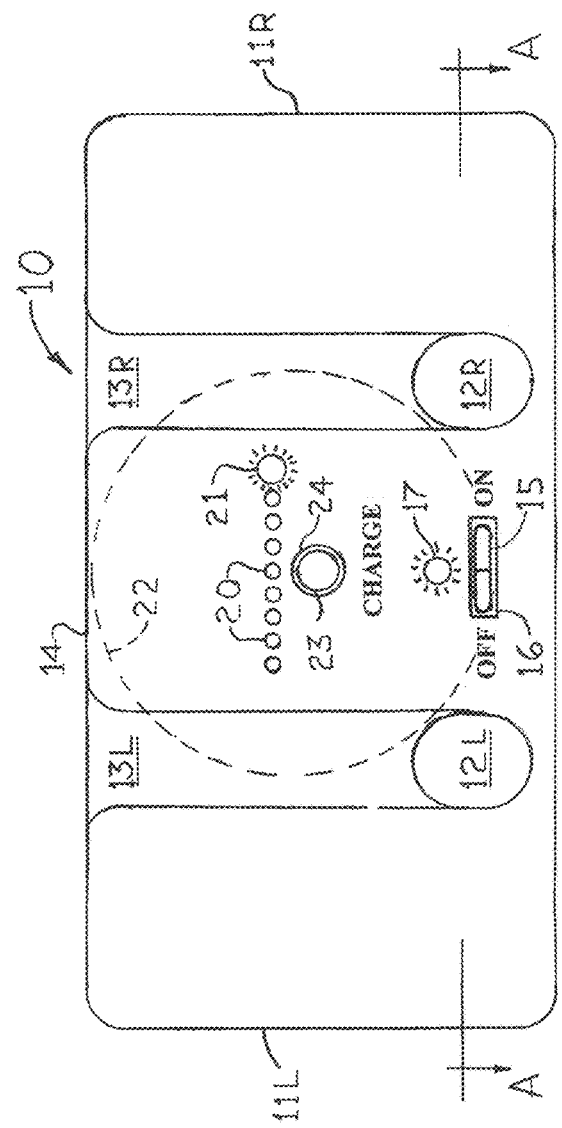
FIG. 1 is a top view of the magnetic TMS device system for the treatment of disorders of the brain or other body tissues or organs.
Figure 2:
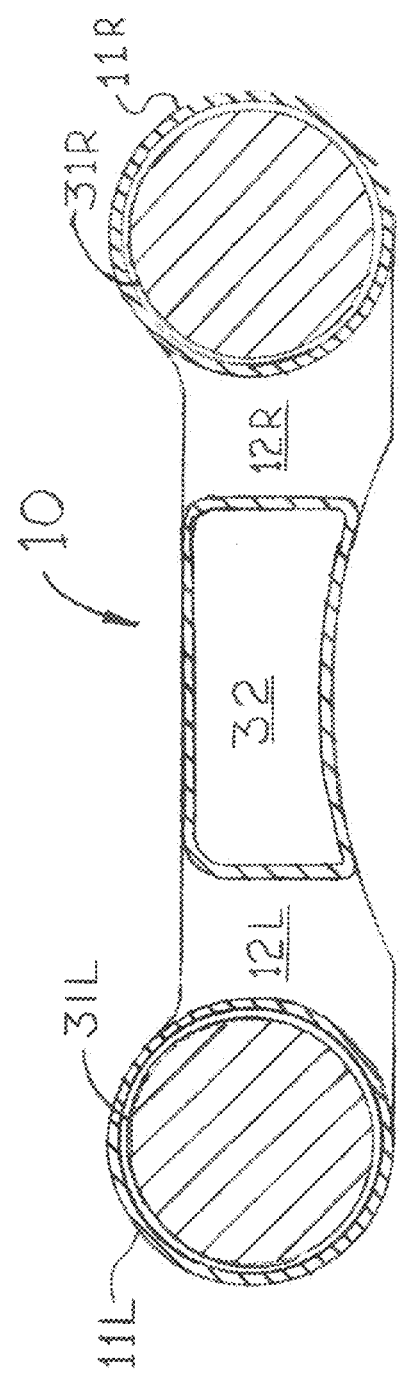
FIG. 2 is a cross section of the TMS device at section "A-A" of FIG. 1.

FIG. 1 is a top view of the TMS device 10 having a left cylindrical portion 11L and a right cylindrical portion 11R around which portions the patient will hold the TMS device 10. FIG. 2 is a cross section of the TMS device 10 at section "A-A" of FIG. 1. As seen in FIG. 2, within the left cylindrical portion 11L is the left capacitor 31L and within the right cylindrical portion 11R is the right capacitor 31R. The top view of the TMS device 10 also shows the left fingers groove 13L, the right fingers groove 13R, the left thumb hole 12L and the right thumb hole 12R all of which are shaped to provide a comfortable and secure means for the patient to hold the TMS device 10 when she places it on her head for the treatment of a migraine headache. The present invention includes the concept that there will be no thumb holes 12L and 12R so as to provide additional volume interior to the TMS device 10 for the electronic components. In that case, the patient will place her thumb to the side of her fingers or around the body of TMS device 10.

FIG. 1 also shows an ON-OFF switch 15 in an ON-OFF switch recess 16. The ON-OFF switch 15 is used to turn the TMS device 10 on or off. When the ON-OFF switch 15 is pushed downward on its right side, it is in the ON position. When that occurs, an LED light 17 turns on to indicate that the TMS device 10 has been turned on. It would be typical for the LED light 17 to have an amber or green color to indicate that the device is ready to charge its capacitors 31L and 31R. The ON-OFF switch 15 would be pushed down on its left side to turn the TMS device 10 off. The ON-OFF switch recess 16 is provided to decrease the possibility that the ON-OFF switch 15 would be inadvertently turned to its ON state. The recess placement of the ON-OFF switch 15 also disallows it being turned off when the ON state is desired.

As seen in FIG. 1, the top surface of the TMS device 10 would also have a capacitor charge switch 23 to cause the battery (not shown) to begin the charging of the capacitors 31L and 31R. The capacitor charge switch 23 would be within the charge switch recess 24 so that it is under the top surface of TMS device 10 to prevent the accidental pushing of the capacitor charge switch 23. By having both switches 15 and 23 on the top surface of the TMS device 10 placed respectively within the recesses 16 and 24, accidental actuation of either of the switches 15 or 23 would be prevented. This is particularly important to prevent the TMS device 10 from being inadvertently turned on when it is placed inside a woman's handbag.

When the capacitor charge switch 23 is pushed down to charge the capacitors 31L and 31R, a series of LED lights called the capacitor charging lights 20 will illuminate in sequence to indicate that the capacitors 31L and 31R are being charged. The optimum color for the capacitor charging lights 20 is probably amber which indicates that the patient should get ready for the (preferably) green LED capacitors charged light 21 to turn on which indicates that the capacitors 31L and 31 have been fully charged and are ready to be discharged into the spherical cap coil 22. The circular outline of the spherical cap coil 22 is shown by dotted lines in FIG. 1. The sequence of lighting the LED lights 20 could be on a timed basis or they could be triggered by the capacitors 31L and 31R reaching a specific and increasing voltage. An example of the time dependence of the lighting of the capacitor charging lights 20 would be if it would take 40 seconds to charge the capacitors 31L and 31R and if there were exactly ten capacitor charging lights 20, then each additional amber LED light 20 could come on at 4 second intervals until all ten of the capacitor charging lights 20 were turned on. When the last amber LED light 20 would light, (that LED light 20 next to the green LED light 21) then simultaneously the green capacitors charged light 21 would come on, or the capacitors charged light 21 could come on 4 seconds after the last amber LED light 20 comes on. In either case, when the green LED light 21 would come on, that indicates that the capacitors 31L and 31R have been fully charged. It should be understood that each of the LED lights indicating that the capacitors 31L and 31R are being charged could be first flashing and then go on steady and then the next LED light would flash until it went on steady. As few as one such LED to first flash then go on is conceived of as part of the present invention or as many as 10 LED lights to first flash then stay steady on is also conceived of for this invention.

Once the capacitors 31L and 31R are fully charged, they are ready to be discharged into the spherical cap coil 22 to create the intense magnetic pulse to treat a migraine headache. As an additional indication to the patient that the capacitors 31L and 31R have been fully charged, a sound generator (not shown) within the TMS device 10 would create a sound that would last from as short as 0.001 second to as long as 2 seconds as an additional indication to the patient that the capacitors 31L and 31R have been fully charged. An optimum sound would last approximately 1±0.5 second and would have a pleasant single tone or it could be a musical type of sound.

In one embodiment, once fully charged the TMS device could begin a count down such as is seen on self-timers on cameras where the green LED 21 would flash slowly at first then faster then go solid on, then the pulse would be delivered. A soft tone or a clicking sound that would not aggravate the patient's headache could by itself or with the LED utilize the same pattern of speeding up, then going steady just before the pulse is delivered. In this way, once the pattern begins, the patient need only place the TMS device in the appropriate place on her head and wait until the pattern stops, the green LED 21 stays continuously on and the pulse is delivered.

FIGS. 1, 2 and 4 indicate the novel means that the TMS device 10 would utilize for the patient to hold that device against her head for the treatment of a migraine headache or any other disorder originating from her brain or any other part of her body. It should be understood that the TMS device 10 could be used to apply a magnetic pulse to any part of the human body where the application of that magnetic pulse could be effective in the treatment of some medical problem.

FIG. 2 is the cross section of the TMS device 10 at section "A-A" of FIG. 1 showing the left cylindrical portion 11L, the right cylindrical portion 11R, the left capacitor 31L, the right capacitor 31R, the left thumb hole 12L, the right thumb hole 12R, and an electronics and battery section 32. FIG. 4 is a partial side view shown from the back of the TMS device 10. From these three figures (FIGS. 1, 2, and 4) it will be apparent to a person of ordinary skill in this art that this is a novel and efficient means for the patient to securely and comfortably hold the TMS device against her head for the treatment of a migraine headache. It should also be understood that the TMS device 10 could be conveniently held without the need for thumb holes 12L and 12R.

From FIGS. 1 and 4 it is clear to see that as many as four of the patient's fingers (other than her thumb) of her left hand could be placed in the left fingers groove 13L and the right hand fingers could be simultaneously placed in the right fingers groove 13R. At that same time, FIGS. 1 and 2 show that the patient's left thumb could be placed through the left thumbhole 12L and her right thumb could be placed through the right thumbhole 12R. This novel and useful means for holding the TMS device 10 allows the patient to place the TMS device 10 securely onto her body wherever treatment with a strong magnetic pulse would ameliorate some health problem. Most importantly, placement of the TMS device 10 onto the patient's head or neck would be for the treatment of a migraine headache.

An important and novel feature of the present invention is the absence of a switch to trigger the discharge of the capacitors 31L and 31R into the spherical cap coil 22 to create an intense, short time duration, magnetic pulse. This TMS device 10 would be designed to have the patient place the device on her head for the treatment of a migraine headache at some reasonable time (greater than 2 seconds) after the capacitors charged light 21 is turned. A time period of about 7±1 seconds after the LED green light 21 comes on would be an optimum time period for the patient to comfortably place the TMS device 10 onto her head. At that time, the electric current in the spherical cap coil 22 would produce the desired intense magnetic pulse. The maximum pulse intensity at the center of the spherical cap coil 22 should be greater than 0.2 Tesla and optimally the maximum pulse intensity should be 1.0±0.5 Tesla. The pulse rise time should be between approximately 100 and 300 milliseconds with an optimum time being 190±10 milliseconds.

Although it is understood that a 7 second time delay may be optimum, it should be understood that any time period between approximately 2 and 60 seconds could be used as a time interval from the time that the LED light 21 goes on until the magnetic pulse is actuated to treat the patient. Any time period that is less than approximately 2 seconds would be too short a time interval for the patient to feel comfortable in getting the TMS device 10 properly placed onto her head.

A very important design feature of the present invention is that a sound would be created by the TMS device 10 at the same time that the TMS pulse is delivered. This sound could last for a time period between 0.001 second and 2 seconds with an optimum time being approximately 1±0.5 seconds. The importance of this sound is that it indicates to the patient that a magnetic pulse that is within the specified intensity limits for the TMS device 10 has been delivered. If either the amplitude or the pulse rise time of the TMS delivered by the spherical cap coil 22 is not within its specified limits, then no sound will be created and the patient will know to contact the manufacturer to obtain a new TMS device 10. The detection of pulse amplitude and pulse rise time will be made by a small coil placed at or near the center of the spherical cap coil 22.

An additional feature of the present invention is to "pot" the coil 22 by encapsulating it in plastic. This will reduce the noise produced by wire movement in the coil when it is energized to deliver a pulse. Potting the coil also prevents unwanted motion of the wires of the coil 22, resulting in improved longevity for the coil.

After the magnetic pulse is actuated, the device will remain in the ON condition but the LED lights 20 and 21 will go to an off condition. The patient can get another pulse by once again pressing the capacitor charge switch 24, the LED lights 20 will then illuminate sequentially approaching the green LED light 21. When the light 21 is illuminated, the timing circuit will start the time period to cause the magnetic pulse to occur. When the patient takes the last of a sequence of magnetic pulses, she will press down on the left side of the ON-OFF switch 15 to turn off all the circuits of the TMS device 10.

FIG. 3 is a front surface view of the TMS device 10 and FIG. 4 is a partial view of the back surface of the TMS device 10. FIG. 3 shows a battery needs recharging light 18 that would indicate to the patient when the battery in the TMS device 10 will need to be recharged. It would be typical for the battery in the TMS device 10 to have a sufficient capacity to provide about twenty magnetic pulses. An optimum LED light 18 would be a light that flashes on and off at about a 0.5 second period when there is enough capacity left in the battery to provide between 5 and 8 magnetic pulses. The battery needs recharging LED light 18 would remain steadily on when there would be between 1 and 4 pulses remaining before the battery is completely discharged. That LED light 18 would remain on if there was no capacity left in the battery and the ON-OFF switch 15 was in the ON condition. It is also understood that the LED light 18 could have a red or any other color that would signify the need for the battery to be recharged. Recharging of the battery within the TMS device 10 would be accomplished by means of a separate recharging device (not shown) that includes an AC-to-DC convertor and wire with plug (not shown) as is typically used to recharge any portable device such as a cell phone or a tablet. Such a recharging device would have a plug that would fit into the battery recharge receptacle 19 that is shown in FIG. 3. It is also envisioned that a multi-segment LED battery indicator could be used instead to show the battery state as is done on digital cameras and cell phones.

It is also envisioned that an alternative version of the TMS device 120 would have all the control on the Front Surface as shown in FIG. 3A. This simplifies the TMS device by putting all the display and buttons together on a single surface and orients them in such a way as to minimize the potentially damaging effects of the magnetic pulse. Specifically, there is now a single power button 121 that initiates a power on and charge cycle and after a pulse is delivered, stays active for a specified period to allow initiation of a next pulse. If not activated, the TMS device 120 would turn off completely to save battery. The front of the TMS device 120 also includes a battery charge indicator 123, a race track of LEDs 122 that light sequentially as the capacitors charge and two pulse activation buttons 125L and 125R either or both of which will deliver the pulse and are designed to be pressed with the patient's fingers or thumbs as they hold the device against their head. A light or LED 128 with the Rx symbol is also on the front to ensure that the patient knows they have pulses remaining on their prescription. When the prescribed number of pulses have been depleted below a predetermined threshold, or when the prescription is within a pre-set period from expiration, the light 128 would flash or remain lighted to notify the patient. The light 128 could be a red, green or amber LED or it could be a single color that is solid on when pulses are available, off when not and flashes when near the limit.

A light or LED 128 with the RX symbol next to it is also on the front to ensure that the patient knows they have pulses left on their prescription. As the pulses near the limit, or when the prescription is within a pre-set period from expiration, the light 128 would flash to notify the patient. the light 128 could be a red/green LED or it could be a single color that is solid on when pulses are available, off when not and flashes when near the limit.

Other display icons that are on the front surface are the child lock display 127 that is activated by a hidden switch near the SIM card slot (not shown). A temperature icon 129 would show if conditions are too hot or too cold for use. An AC power indicator 124 would show when the device is charging and could flash during charging, turn solid when done. Finally a call customer service icon 126 would provide notification that the device has experience an internal failure of hardware or software and could also indicated to call when the prescription is running out or has run out.

FIG. 4 is a partial view of the back of the TMS device 10. As described above, FIG. 4 shows the left finger groove 13L and part of the right finger groove 13R. It is into these grooves that the patient could place 3 to 4 fingers (but not the thumb) to securely hold the TMS device 10 when it is placed onto the patient's head. FIG. 4 also shows the prescription refill needed LED 31 that would flash with a time period of approximately 0.5 seconds when there are only approximately 17 to 30 pulses still available before the doctor must provide a refill prescription or only 14 to 8 days remaining until the end of the time period during which time the TMS device 10 would remain operable. The prescription refill needed light 31 would remain steadily on when there are 16 or fewer pulses remaining before the TMS device 10 becomes inoperable or there are only 7 or fewer days left until the TMS device 10 becomes inoperable. With these warnings, the patient would know that she must contact her doctor to receive a refill prescription.

The prescription refill port 33 is used by the patient to accommodate a refill of her prescription for magnetic pulses, which refill prescription must come from her physician or any other person legally entitled to write a prescription. Unlike other refill prescriptions written on a piece of paper that a patient could typically receive from a doctor to obtain an additional dose of pills, the refill prescription for the TMS device 10 would be delivered electronically or by means of radio frequency (RF) communication or by means of a SIM card that is placed into the TMS device 10 through the port 33. The SIM card can also be used to provide a unique serial number for each patient. In that case, each and every TMS device 10 would be identical with its unique serial number being provided by the SIM card.

A refill prescription for each patient would increase the number of pulses as prescribed by the patient's doctor and would also extend the time period during which the device will remain in a condition where it can be turned to its ON state and can be used to deliver a magnetic pulse. As an example, if a patient would have four migraine headaches each month and would use ten magnetic pulses to treat each headache, then she would use forty pulses per month and 240 pulses in a six-month period. For such a patient, a physician might prescribe 250 pulses over a six month period with the TMS device 10 going to its off condition if either the 251st pulse was requested or the 6 month time period had expired. Before either of those events would occur, the LED light 33 would start flashing and later turn steadily on as a warning to the patient to promptly obtain a refill prescription from her doctor. It would be desirable for the LED light 31 to have a color that is different from the colors chosen for the LED lights 17, 20 and 21. It could be desirable for the LED lights 18 and 31 to have the same color, as each would indicate to the patient that some action must be taken.

FIG. 4 also shows a battery access door 34 that could be opened to access the battery (not shown). In this way, a failed battery could be readily replaced. It is typical for a device such as the TMS device 10 to have its battery fail prior to any other part of the device failing. Therefore, an easy means to accomplish battery replacement would be highly desirable.

Figure 5:
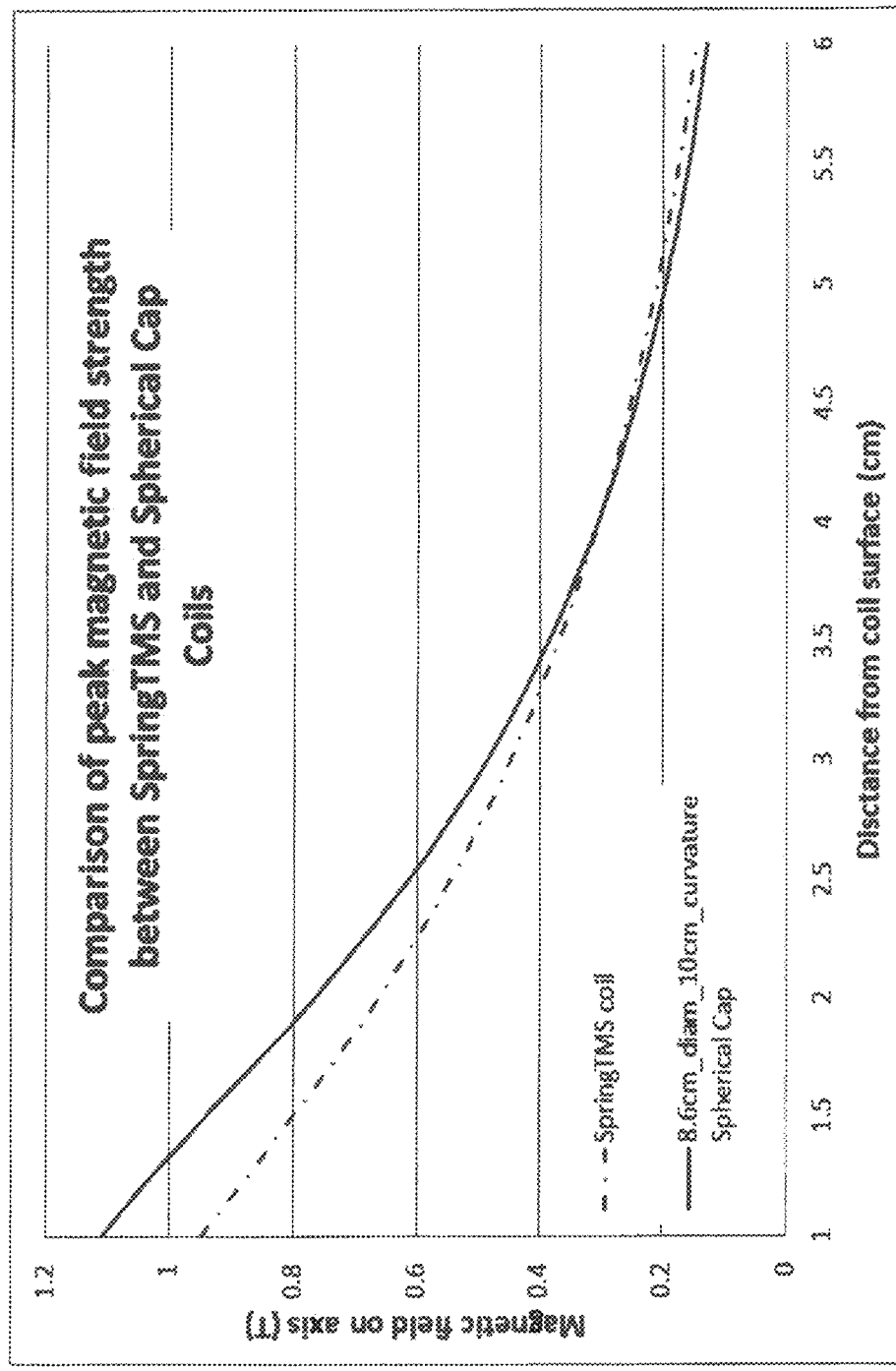
FIG. 5 illustrates the fall of magnetic field strength with distance from the center of the Spring TMS coil and the center of the spherical cap coil.

FIG. 5 shows the falloff of magnetic field intensity as a function of distance from the bottom surface of the spherical cap magnetic coil as compared with that same magnetic field intensity for a prior design (the Spring TMS device) that has an elliptically shaped magnetic coil. This field strength measurement indicates that a smaller, lighter, aluminum wire coil can produce essentially the same magnetic field strength as compared to a heavier, elliptically shaped, copper coil that has been used in a prior art design TMS device. It is urgently important that the magnetic coil 22 be potted in plastic to extend its useful life and to avoid the sound that might otherwise emanate from the coil 22 if the wires were free to move. Details of the design of such a coil potted in plastic is explained below with the assistance of FIGS. 10 and 11.

Figure 6:
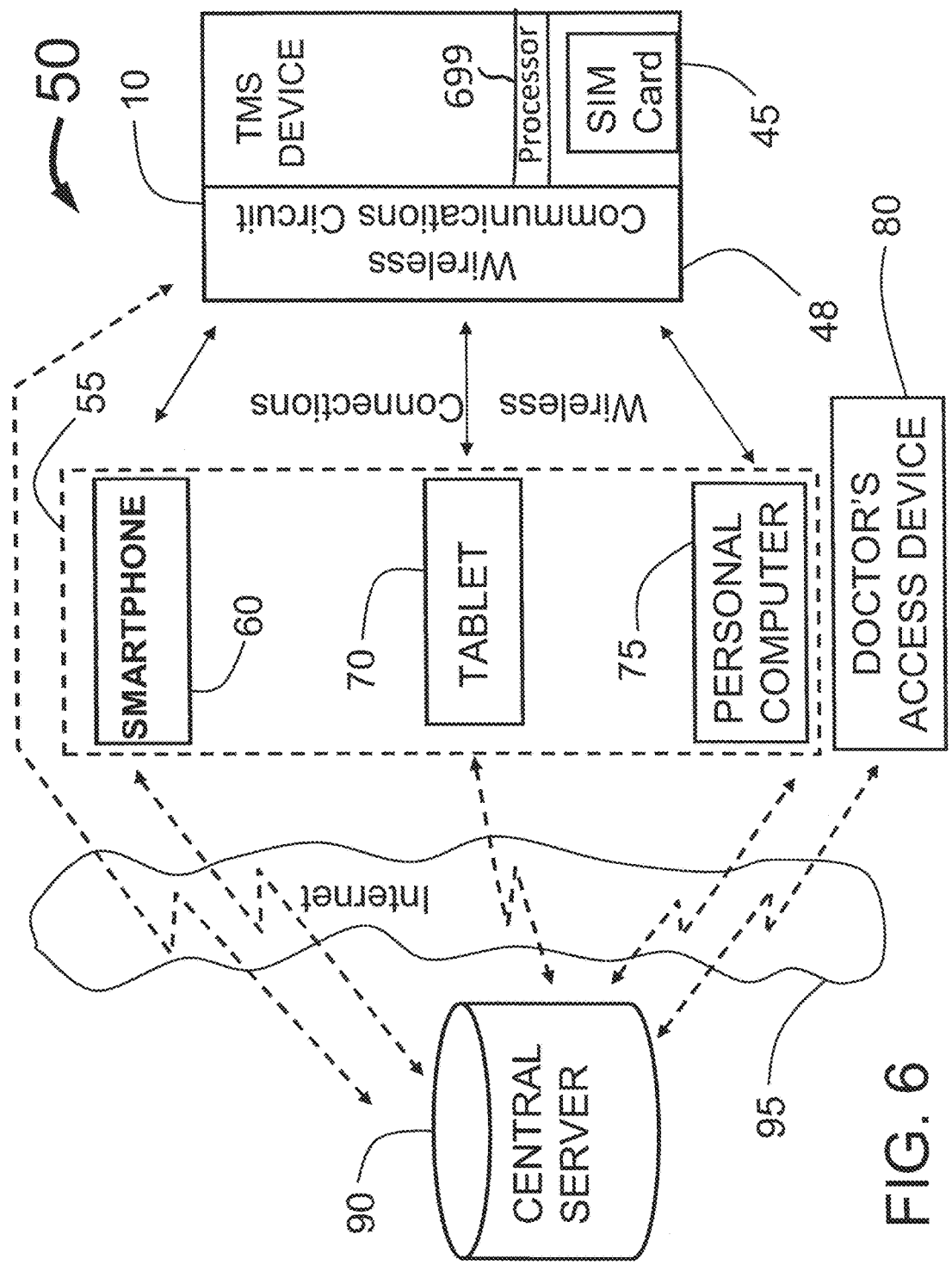
FIG. 6 is a flow chart showing the flow of information among the various portions of the TMS system to provide a refill prescription for a migraine patient.

FIG. 6 is a block diagram of the TMS device system 50. The system 50 includes a computational device 55 with Bluetooth data communications capability as well as the ability to connect to the Internet 95. The computational device 55 is kept by the patient and may be, for example, a smartphone 60, tablet 70 or personal computer 75. The system 50 includes the TMS device 10 having a SIM card 45 and wireless circuit 48. The wireless circuit 48 may be cellular wireless data, WiFi (a, b, g or n) or Bluetooth. Bluetooth is a well-known standard for short range data communication between computational devices 55 which include (but are not limited to) personal computers 75, cell phones and tablets 70 and their accessories. Bluetooth and WiFi capabilities are built into most cell phones including smartphones 60 which include i-Phones, Android phones and Blackberry cell phones. Bluetooth communication capability is also built into most tablet computers and personal computers (PCs). Add-on Bluetooth circuits are also available for personal computers 75.

If WiFi is used for the wireless connection, then the TMS device 10 would connect through a local router to the smartphone 60, tablet 70 or PC 75 or directly to the Internet. If the wireless connection is a cellular data connection then no local router is needed and the TMS device 10 can connect through the cellular data network to the Internet.

WiFi or cellular data would allow communication directly between the TMS device 10 and the central server 90 without the need for a smartphone 60, tablet 70 or PC 75. In this case, the TMS device 10 would include the application/program to facilitate downloading new or changed prescriptions and uploading of diagnostic data and patient use data between the TMS device 10 and the central server 90.

The overall electronic circuitry of the TMS device 10 includes a memory storage which may be in the form of a SIM card 45 which is insertable through an exterior cover of the TMS device 10.

The remaining descriptions will describe the procedure of downloading new prescriptions to the SIM card 45 in the TMS device 10 using Bluetooth as the wireless connection although similar functions can be applied if WiFi is used to communicate between the TMS device 10 and a smartphone 60, tablet 70 or PC 75.

Typically, the prescription information, number of pulses or time remaining (and/or used), patient use information and device diagnostic information would be stored in flash memory on the SIM card 45. Patient use information would include, for example, the time and date for each pulse delivered by the TMS device 10. Device diagnostic information would include (but is not limited to) battery condition, magnetic pulse strength and pulse shape for each delivered pulse, any faults in device operation, etc.

Once a Bluetooth connection between a computational device 55 and an accessory is set-up and enabled for automatic connection, turning on the accessory power within range of the Bluetooth antenna in the computational device 55 will automatically cause the connection to be established.

The system 50 also includes a central server 90, which includes patient prescription information and can also be used to keep patient use information and diagnostic information uploaded from the TMS device 10. The central server 90 is also connected to the Internet 95.

The system 55 also includes a doctor's access device 80 which can connect through the Internet 95 to the central server 90. This would allow the patient's doctor or his staff (nurse practitioners or professional assistants) to write prescriptions for additional time to remain active and additional pulses for the TMS device 10 which when transferred to the SIM card 45 on the TMS device 10 will provide the patient additional time (e.g. 6 months) or pulses (e.g. 300 pulses) to be used to treat the patient's migraine headaches. The doctor's access device 80 could also access patient use information and diagnostic information downloaded from the TMS device 10 to the central server 90. The doctor's access device 80 can be a personal computer, tablet or smartphone that has Internet connectivity and a browser that allows standard Internet access. Access to write prescriptions on the central server 90 can be through html or other web pages or with a specific program that can run on the doctor's personal computer or an APP that can run on the doctor's smartphone or tablet. Appropriate security with appropriate login and passwords would be required to allow prescriptions to be written. This security could be obtained by using a specific serial number for the TMS device 10, which serial number could originate from the SIM card 45.

It is also envisioned that the central server 90 would have the ability to communicate the writing of a new prescription to the patient's insurance company for reimbursement or to bill the patient's credit card. An e-mail indicating that a new prescription is available can be sent to the patient including a receipt for payments if the patient is paying or confirmation of insurance reimbursement if the insurance company is paying. A phone call or SMS message (standard text message) could also be used to notify the patient.

FIGS. 7A through 7E inclusive illustrate features of a smartphone 60 that would be one of the means to write new prescriptions into the patient's TMS device 10. The smartphone 60 has a main button 69 to download a new prescription from the central server 90 to the TMS device 10 as well as upload patient use and device diagnostic information from the TMS device 10 to the central server 90.

Once the patient knows that a new prescription to provide additional time and/or additional pulses for the TMS device is ready to be sent to her, she can download the prescription to the SIM card 45 on her TMS device 10 in the following way:

1. Assuming the smartphone 60 is turned on, turn on the TMS device 10, which connects via Bluetooth to the smartphone 60.
2. Initiate the TMS APP. For most smartphones 60 and tablets 70, one simply touches the TMS APP icon 61 shown in FIG. 7A.

Once the APP 61 is touched, it will do everything needed to download the doctor's prescription into the TMS device 10 and upload patient use and device diagnostic information from the TMS device 10 to the central server 90. In this example, the first thing the APP 61 does is to confirm that the Bluetooth connection between the smartphone 60 and the TMS device 10 is active. When that connection is made, the smartphone 60 would display the "TMS DEVICE CONNECTED" 62 notification as shown in FIG. 7B. Next the smartphone 60 will indicate connection to the central server 90 by means of the Internet. This can be done using cellular data connections or through local Wi-Fi connection. All modern smartphones 60, tablets 70 or personal computers 75 have such a cellular data or Wi-Fi connection capability. The connection will involve a login process that will use patient and device information stored on the SIM card 45.

Figure 7E:
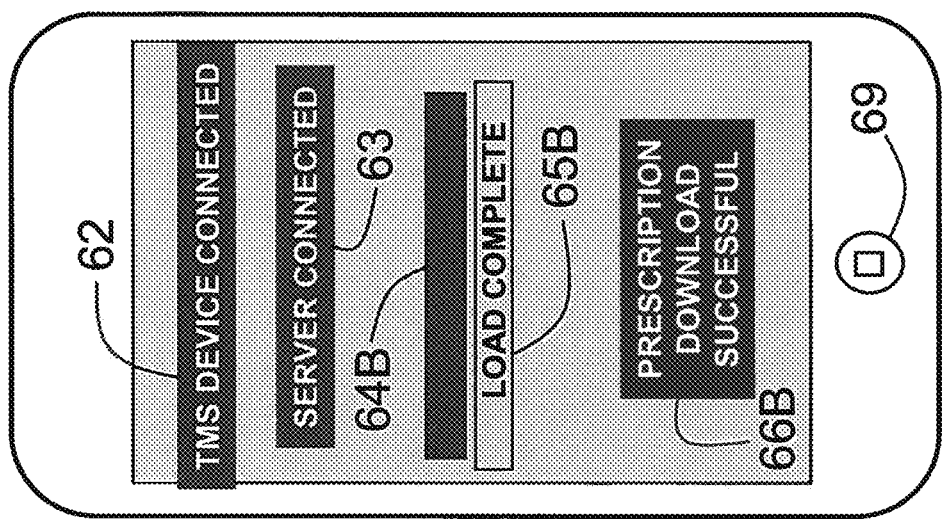
FIG. 7E shows the wording that would come up on the smart phone showing that a prescription download has been successfully placed into the TMS device.
Figure 7D:
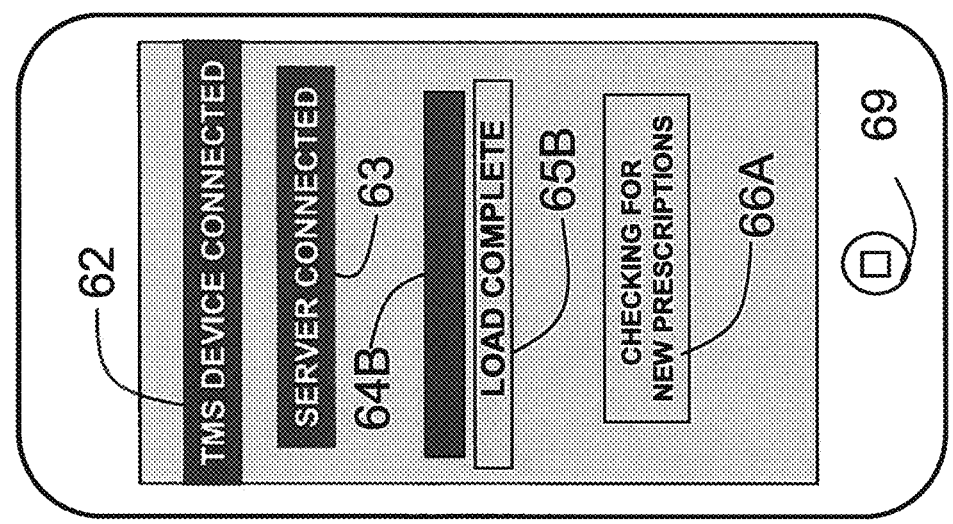
FIG. 7D shows the wording that would come up on the smart phone showing that the loading of the server has been completed and the smart phone is checking to see if there is a new prescription for the patient.
Figure 7C:
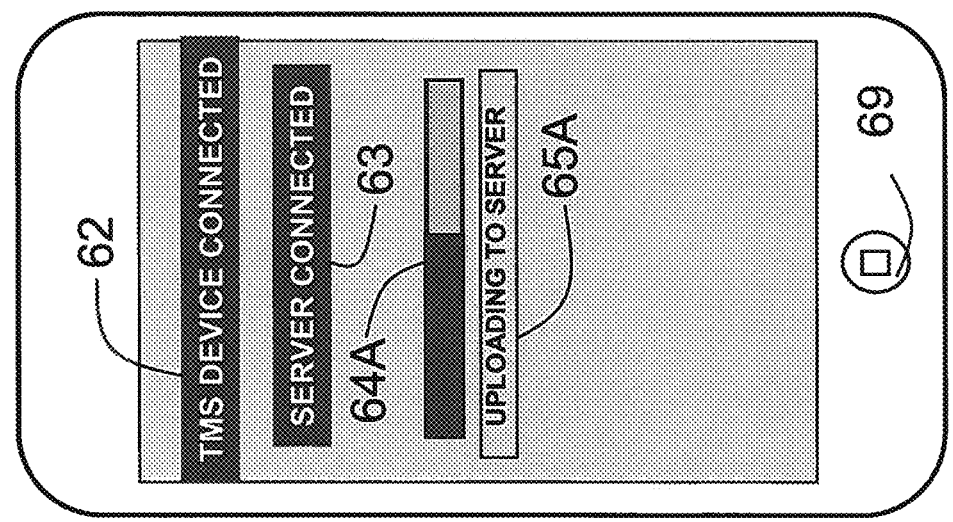
FIG. 7C shows the wording that would come up on the smart phone showing that the central server is being connected to the TMS device.

Once connected, the "SERVER CONNECTED" 63 message will appear on the smartphone 60 as shown in FIG. 7C. The scrollbar 64A and "UPLOADING TO SERVER" 65A message will then immediately appear. The scrollbar 64A will display the progress of the upload of patient use and device diagnostic data by motion to the right as is typical for many computer programs and APPs. When the scrollbar 64B is completely filled, the message "LOAD COMPLETE" 65B will be displayed as shown in FIG. 7D.

The next and last step would then begin with the message "CHECKING FOR NEW PRESCRIPTIONS" 66A shown in FIG. 7D. The APP 61 would then securely download the new prescription information to the TMS device 10 through the Bluetooth connection where the information would be stored on the SIM card 45. Upon completion of these actions, the message "CHECKING FOR NEW PRESCRIPTIONS" 66A would disappear and the message "PRESCRIPTION DOWNLOAD SUCCESSFUL" 66B would appear as shown in FIG. 7E. At this point pressing the main button 69 would return the smartphone 60 to the configuration and screen display as shown in FIG. 7A.

Of course it is envisioned that while the description above has every part of the process being successfully completed, there would be appropriate error messages and help screens in the case of there being a problem. Such messages could include "TMS DEVICE NOT FOUND" with instructions to make sure it is close enough and turned on and that the Bluetooth connection has been previously made. Ideally, the initial Bluetooth connection is made with help by a nurse in the doctor's office. Similarly a message "SERVER NOT FOUND" followed by information telling the patient why, would be a possible presentation. Such reasons could include the messages "WIFI DATA DISABLED," "CELLULAR DATA DISABLED" where the patient needs to go to their settings to allow Internet data connectivity. Other reasons could be "NO WIFI AVAILABLE" or "NO CELLULAR DATA AVAILABLE". In addition, if the prescription is not available, instead of message 66B, the smartphone 60 would display "PRESCRIPTION NOT AVAILABLE, CHECK WITH YOUR DOCTOR".

An APP on a tablet 70 or a program that runs on a personal computer 75 would do essentially the same thing as the APP 61 disclosed for use with the smartphone 60 as shown in FIGS. 7A-7E inclusive.

While we have described the process for data communication between the TMS device 10 and the central server 90 as initiated by an APP 61 on a smartphone 60, it is also envisioned that the APP/program could reside on the TMS device 10 itself. In one example, it would be on the SIM card 45, itself. If the APP/program is on the TMS device 10 then once the Bluetooth connection is established, the APP/program could run automatically on the computational device 55. Such "Autorun" capability is well known.

It is also envisioned that if the TMS device 10 connects directly to the central server 90 through WiFi, a phone line with a modem wired Ethernet connection or a cellular data connection, that the TMS device 10 would initiate the process described above for downloading and uploading. If the TMS device 10 has an alphanumeric display it could also display the status messages described above for use on a smartphone.

Figure 8:
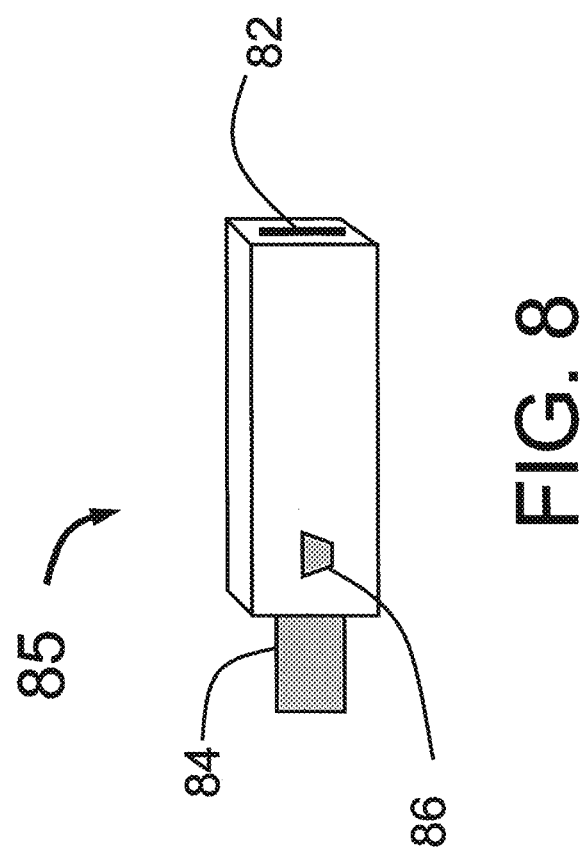
FIG. 8 illustrates an adapter that allows a SIM card to be connected to the TMS device's USB interface.

FIG. 8 shows a schematic view of an adapter 85, which provides an alternative means to communicate information between the central server 90 of FIG. 6 and the TMS device 10. In this case, the SIM card 45 (depicted in FIG. 6) would be removed from the TMS device 10 and inserted into the slot 82 in the adapter 85. The USB plug (male) connector 84 of the adapter 100 can then be inserted into a USB receptacle (female) connector in a personal computer 75. If the SIM card 45 or adapter 85 has autorun software on it, then the process for connecting to the central server 90, uploading data from the SIM card 45 and downloading new programs would proceed much as it does as shown in FIGS. 7A-7E. If autorun is not used, then the patient would start a program on their personal computer 75 which would do the same thing.

The adapter 85 is also designed to work with smartphones 60 or tablets 70 that may not have a USB connector. The female mini-USB connector 86 allows the adapter 85 to be connected through a cable (not shown) to a smartphone 60 or tablet 70. For example the cable could have a male mini-USB connector on one end to connect to the mini-USB receptacle 86 and an iPhone male connector on the other. Once connected to a smartphone 60 or tablet 70 an APP 61 as shown in FIGS. 7A-7E could be used to communicate between the SIM card 45 and server 90 or, as described above for the personal computer autorun process, the APP 61 function could reside on the SIM card 45 or in memory on the adapter 85 which would then run automatically on the smartphone 60 or tablet 70 when connected.

It is also envisioned that instead of the mini-USB receptacle (female) connector 86, a standard or micro-USB connector or other type of connection socket could be used. Finally, the adapter 85 might not have the receptacle 86 but come with cables with USB receptacle connectors that would allow one to connect the USB plug connector 84 to smartphones 60 or tablets 70.

Figure 9:
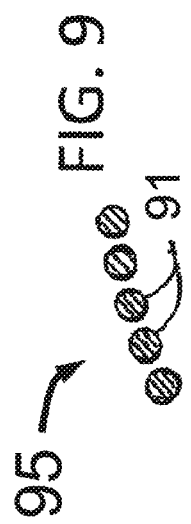
FIG. 9 is a cross section of a portion of a conventional magnetic coil using wire with a circular cross section.

FIG. 9 illustrates a cross section of a limited portion of a prior art magnetic coil 90 that employs wires 91 having a circular cross section. Without being encapsulated in a plastic material, these wires 91 can move when a high amplitude of electrical current (typically several thousand Amperes) passes through them. Such motion can damage the insulation on these wires 91 and also the wire movement can cause an unpleasant sound that can be annoying to a migraine patient.

Figure 10:
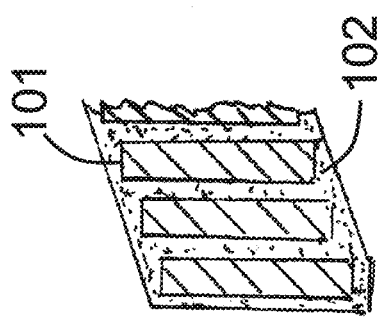
FIG. 10 is a cross section of a portion of a potted magnetic coil formed from wire with a rectangular cross section, the wires being encapsulated in a plastic material.

FIG. 10 is a cross section of a magnetic coil 100 having rectangular wires 101 that is encapsulated in a hard plastic material 102. There are many advantages to such a design, especially when the metal of the coil 101 is a purified aluminum that is anodized to have an insulating, aluminum oxide exterior surface to further guarantee that none of the wires 101 will be electrically shorted against any other wire. An optimum design for the wire 101 would have the wire thickness being approximately 60±40 mils and the length of the rectangle being 200±100 mils. Having the plastic encapsulation 102 used to prevent any motion of the wires 101 relative to each other as well as acting as a further insulation between the wires 101 will guarantee no relative motion between the wires 110. Still further, with the encapsulation attaching the bottom surface of the coil 100 to the case of the TMS device 10, this design will prevent any unwanted sound creation from the coil 100 hitting the case of the TMS device 10.

Figure 11:
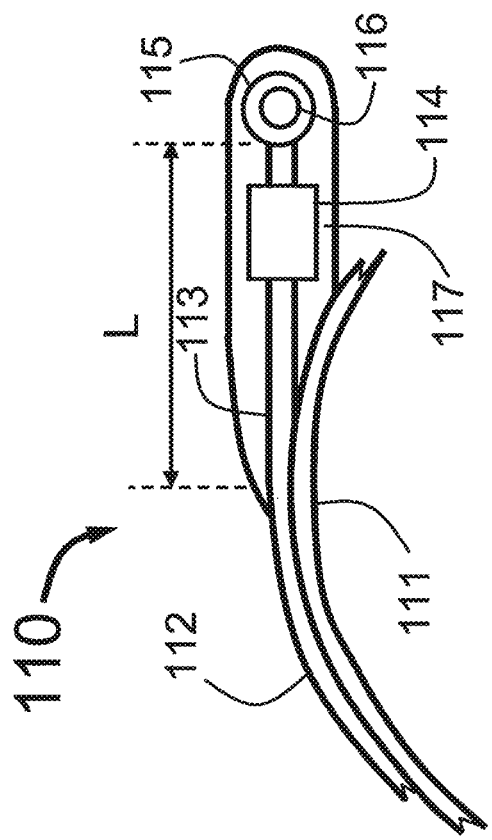
FIG. 11 is a top view of a portion of the magnetic coil showing the immobilization (i.e. encapsulation) of the end segment of the magnetic coil.

FIG. 11 is a top view of part of the outermost turns 111 and 112 of the magnetic coil 110. This design shows the straight wire portion 113 and the electrical connectors 114 and 115 that join one end of the magnetic coil 110 to a terminal 116. A plastic encapsulation 117 can be used to prevent motion of this free end of the coil 110 from being damaged by the motion created by the intense electrical current pulse. This design also prevents the creation of a sound by this electrical connection to the coil 110.

Figure 12:
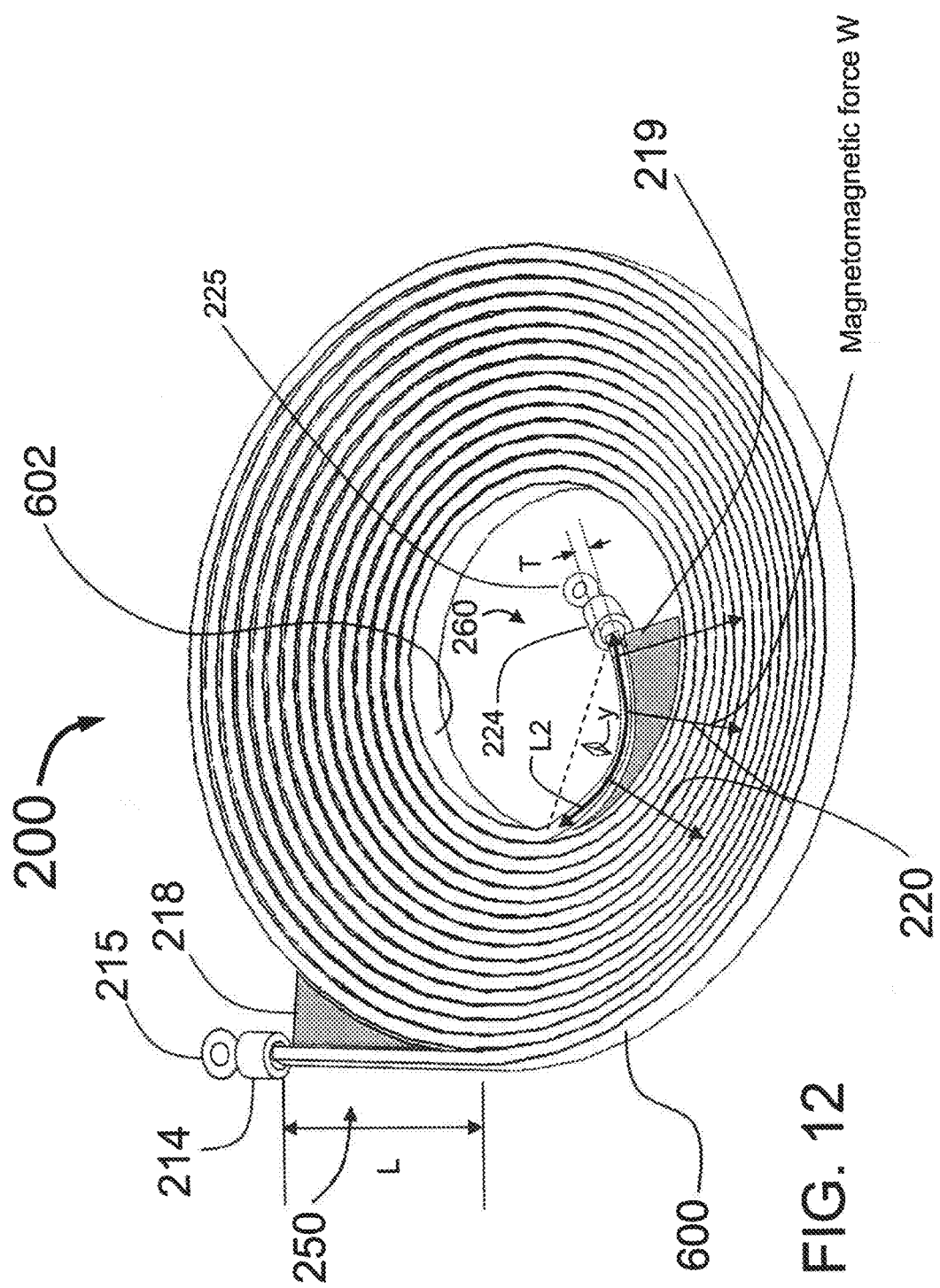
FIG. 12 is a schematic view of another embodiment of the present invention coil with end segments.

FIG. 12 is a schematic view of another embodiment of the present invention coil 200 having an inside or inner section 602 and an outside or outer section 600. The toil 200 has end segments 250 and 260 with corresponding lengths L and L2. Arrows 220 represent the magnetomagnetic force W that is applied to the end segment 260 with y being the maximum distance between a straight line connecting the ends of the curved end segment 260 of length L2. Electrical connectors 214 and 215 are attached to the end connector 250 and connectors 225 and 225 are connected to the end of end segment 260. The end segment stiffeners 218 and 219 are secured or attached to the end segments 250 and 260 to prevent motion of the end segment 250 and 260 during a magnetic pulse. Specifically, for the end segment 260 it can be seen that the magnetomagnetic force W (220) would push the end segment 260 against the stiffener 219 which will prevent it's motion. The stiffeners would typically be made of a relatively high durometer plastic, for example, urothane, kelvar or tecothane.

Stabilization or immobilization of the end segments of the coil that attach to an end connector which attaches to the high voltage circuit board. If left mechanically unsupported or cantilevered, the end segments 250 and 260 can become dislodged from the end connector or cause the connectors 214, 215, 224 or 225 and thus become dislodged from the high voltage circuit board as a result of the magnetomotive forces generated by the delivery of the magnetic pulse. Such stress leads to mechanical degradation and failure and corresponding electrical failure. The maximum stabilization or immobilization of the end segments 250 and 260 of the coil 200 is achieved by minimizing the mechanical bending deflection of the length of the end segments 250 and 260. This length is defined as the distance of the end segment between the point where it separates from the coil body and the point where it terminates electrically. For a simple beam of uniform cross section with moment of inertia I, modulus of elasticity E, length L, with an applied transverse load W, the deflection y at any point x along L is given by the standard formula:

$$y=W*x*(L-x)*[L^2+x*(L-x)]/(24*E*I*L).$$

The greatest deflection occurs at position x=L/2, midspan. For this point the deflection simplifies to:

$$y=(5/384)*(W*(L^3))/(E*I).$$

Thus for a given end segment constructed with given materials and shape properties (which define its moment of inertia I, modulus of elasticity E), the deflection for a given load is proportional to length cubed. The least deflection is achieved with the shortest length end segment 250 or 260. Ideally, the length of an unsupported end segment may preferably be 1 to 5 times, the thickness of the end segment wire in the direction of the magnetomotive force. Under no condition should the length of an end segment 250 or 260 even if supported be more than 20 times, the cross section thickness of the segment in the direction of the magnetomotive force. For example if the coiled wire has a dimension of 0.30 inches in the direction of the magnetomotive force, then the ideal length should be less than 1.5 inches (5×) and under no condition should it exceed 6 inches (20×).

Figure 13:
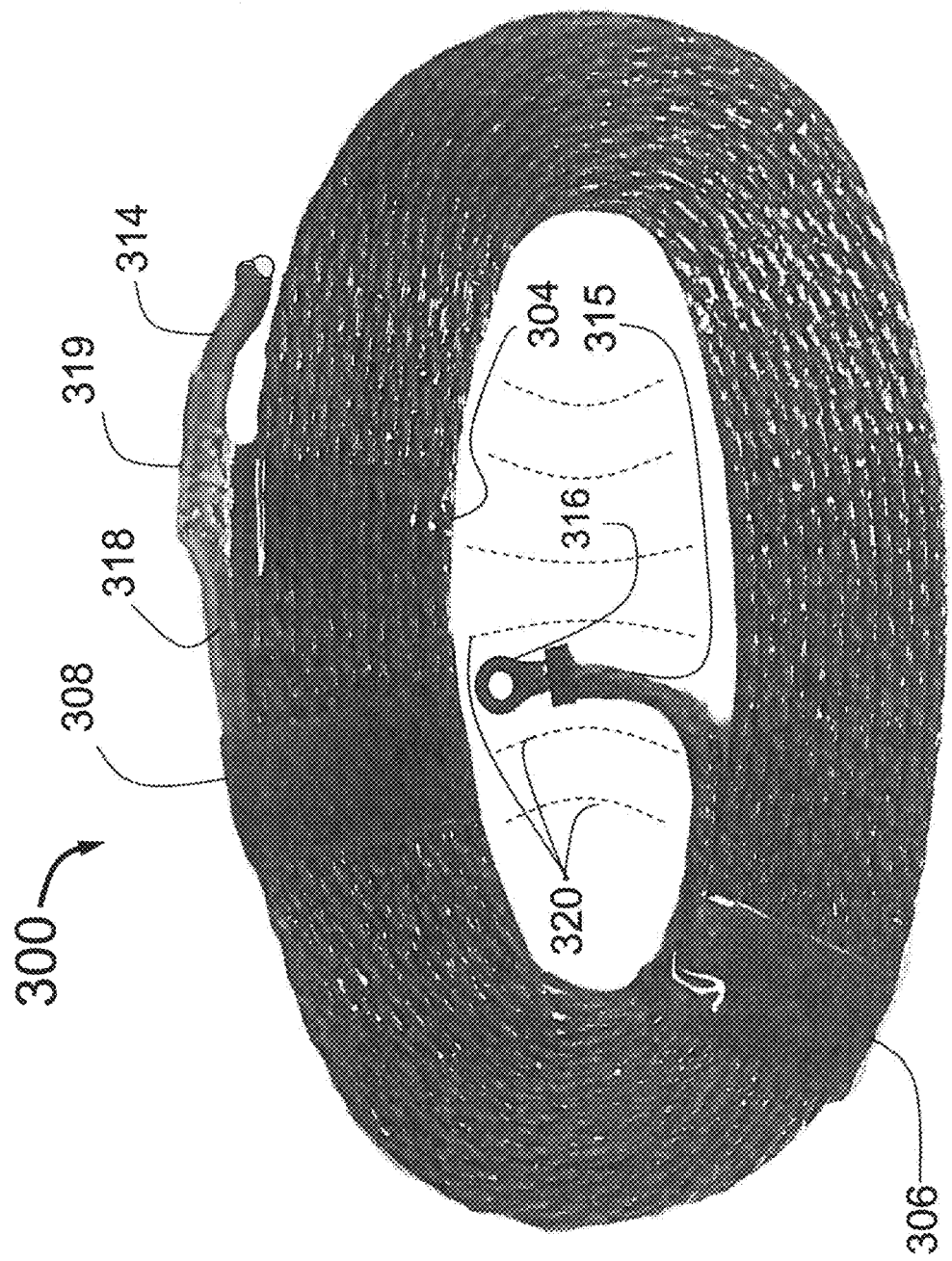
FIG. 13 is a schematic view of yet another embodiment of the present invention coil with the inside end segment parallel to the magnetic field.

FIG. 13 is a schematic view of a generally contoured elliptical coil 300 with inside end wire segment 315 with end connector 316 and outside end wire segment 318 that is attached to the wire 314. The end connector 316 would connect to an electronic circuit board that handles the high voltage circuitry. In another embodiment the inside wire segment 315 could terminate directly into the circuit board without the need for connector 316. The stabilizer bands 306 and 308 hold the end wires 315 and 318 against the wrapped coil 300 to prevent movement. A plastic encapsulation layer 319 covers the distal end of the outside end wire 318 and is held by the stabilization band 304 to keep the end wire 318 from moving with respect to the outside of the coil 300. The magnetic field lines are shown as the dashed lines 320. The present invention coil 300 has the unique feature of having the inside end wire segment 315 oriented approximately parallel to the magnetic field lines 320. This will dramatically reduce the forces induced by the large magnetic field pulse on the inside end wire segment 315 and end connector 316 that could cause the end connector 316 to become detached from the circuit board. This is advantageous in that it will increase the mean time to failure of the TMS device.

Figure 14:
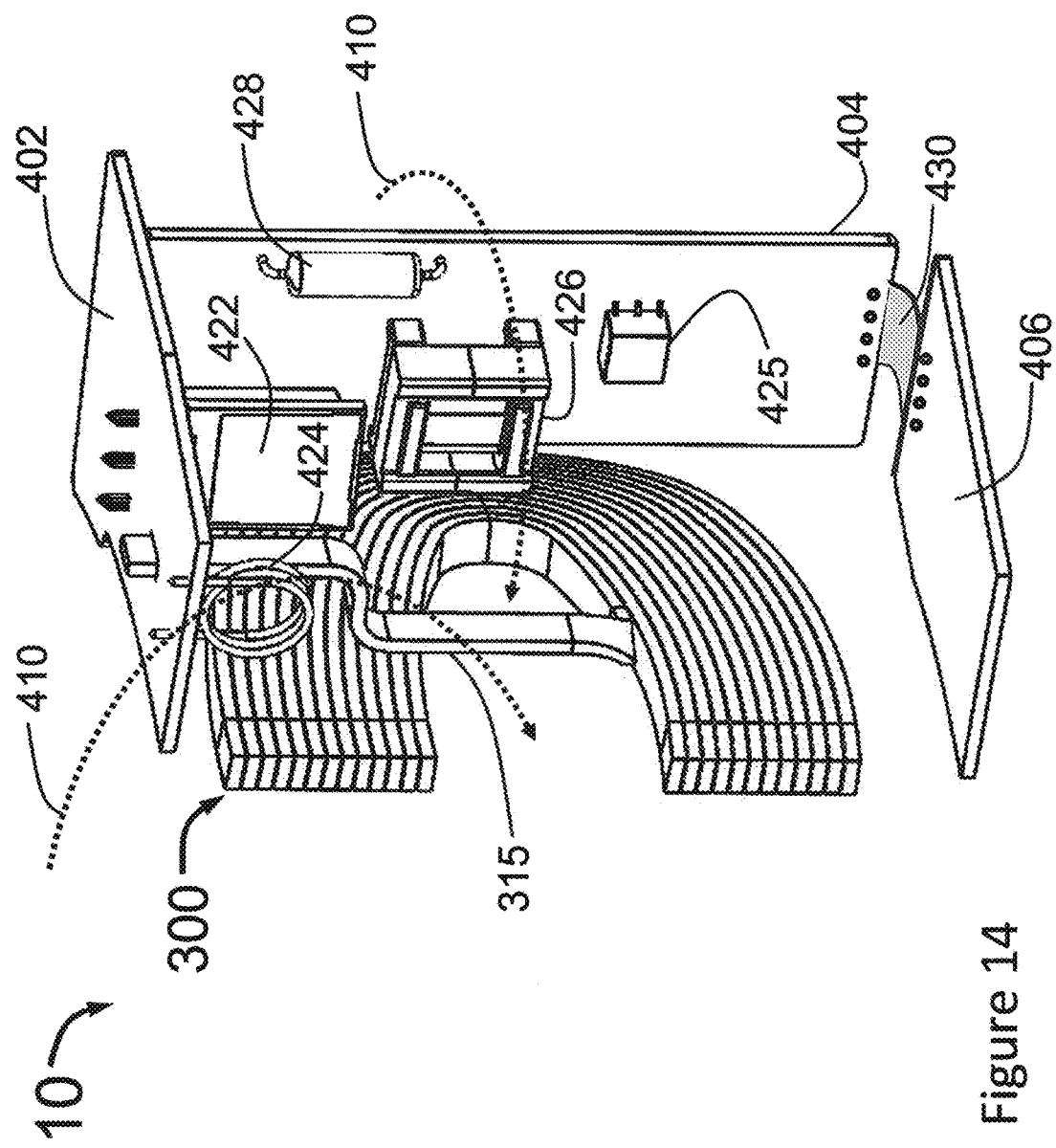
FIG. 14 is a schematic view of printed circuit board layout with component alignments to minimize the forces from the magnetic pulse.

FIG. 14 is a schematic views of the printed circuit board layout of the TMS device 10 with component alignments to minimize the forces from the magnetic pulse from the coil 300.

The aspects of the present invention pertaining to the shape and orientation of wires and components near the TMS coil and on the printed circuit boards within the device include:

1. Orientation and Geometrical Placement of the Printed Circuit Boards:

The arrangement of the invention's circuit boards represented, for example, by (402, 404, 406) with respect to the TMS coil 300 is illustrated in the half-model of FIG. 14. FIG. 14 shows a portion, approximately one-half, of a symmetric geometry. Other printed circuit boards, not shown in FIG. 14, may be similarly symmetrically arranged around TMS coil 300. The arrangement of the printed circuit boards arranged as a box around the approximate circumference of the coil achieves a flatter, mechanically-compact device implementation slightly larger than the width and length size of the TMS coil 300.

2. Orientation of the Inside End Wire 315 Aligned with the Magnetic Field Lines:

The alignment of the coil's inside end wire 315 parallel to the near-by magnetic field flux lines 410 is illustrated in FIG. 14. The coil's outer-lead wire (319 of FIG. 13), not shown, is similarly aligned parallel to the near-by magnetic field flux line 410. The inside end wire 315 and outer lead wire are near-optimally located with respect to the path of the magnetic field to minimize forces between these conductors and the TMS coil 300.

3. Orientation and Placement of the Individual Components on the Printed Circuit Boards:

The electrical components incorporating conductive plates, loops or windings are ideally orientated and placed on circuit boards as illustrated in FIG. 14. Components with conductive plates, for example the power semiconductor 422, are near-optimally positioned and oriented with the plane of the plate parallel to the near-by magnetic field flux lines 410. Similarly, wire-wound component 424 is near-optimally positioned and oriented with the plane of its winding parallel to the near-by magnetic field flux lines 410. Such orientations minimize the repelling forces of the TMS magnetic field. Other major components incorporating internal windings, for example transformers (425 and 426) and wire-wound resistor 428, are ideally orientated and placed on circuit boards as illustrated in FIG. 14. Such components as these are aligned with the plane of their major windings parallel to the flux lines of their near-by magnetic field 410 Such orientation minimizes mechanical forces on these components and reduces their dislodgment.

Figure 15:
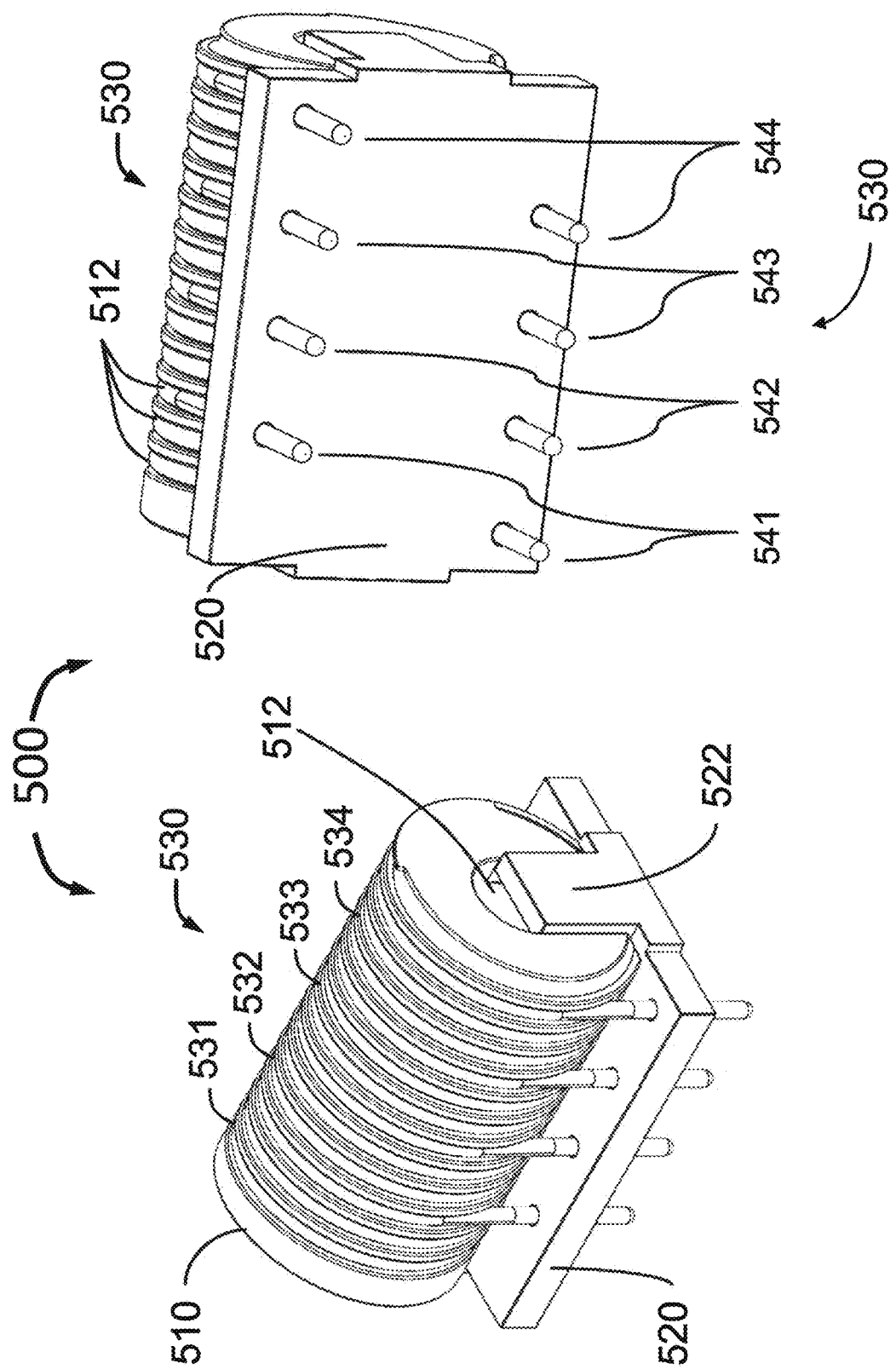
FIG. 15A is a schematic perspective view of a bleed resistor for withstanding large magnetic pulses without breakage.
FIG. 15B is a lower schematic perspective view of the bleed resistor shown in FIG. 15A.

4. Bleed Resistor:

A wire wound component 424 as shown in FIG. 14 is an example of a single resistance element shown in FIGS. 15A and 15B which may have a multi-element bleed resistor.

5. Attachment of Printed Circuit Boards 404 and 406 to Each Other by the Ribbon Cable 430:

These cables are sized in length and soldered directly to the printed circuit boards 404 and 406 in an orientation that maintains a stable shape during magnetic pulses.

6. Additional Encapsulation or Adhesives to Immobilize Wires or Components:
In order to further stabilize wires and other components from displacement due to magnetic pulses, added adhesives (only for example) may be applied for attaching components such as the transformers 425 or 426 to the circuit board 404.

7. Bleed Resistor:
A custom bleed resistor can reliably tolerate thousands of large magnetic pulses without internal breakage.

It is also envisioned that using rigid flex a single unit can be folded into a three dimensional printed circuit board (not shown) forming two or more sides of an open box to reduce the need for connectors between boards such as ribbon cable 430.

It is also envisioned that using 3D printing a single unit three dimensional printed integrated printed circuit board (not shown) forming two or more sides of an open box can be created to reduce the need for connectors between boards such as the ribbon cable 430

FIGS. 15A and 15B are schematic views of a custom bleed resistor 500 to remove residual energy in the coil 300 of FIG. 14 after a magnetic pulse is delivered. The custom bleed resistor 500 shown is capable of withstanding many thousands of magnetic pulses. One embodiment consists of core 510, base 520 and one or more resistor elements 530. FIG. 15A shows an embodiment with four resistor elements 531, 532, 533 and 534. Connecting elements 512 and 522 attach to each other and are used to lock the orientation of core 510 and base 520 together. An alternative embodiment (not shown) has core 510 and base 520 made as a single component. The underside view of the custom bleed resistor shown in FIG. 15B shows the resistor leads 541, 542, 543 and 544 of resistor elements 531, 532, 533 and 534 extending through the base 520. The leads are used to connect each bleed resistor 530 to a printed circuit board as shown with a single resistor element 424 as shown in FIG. 14. The printed circuit board can connect resistor elements 530 in series or parallel to achieve desired combinations of resistance and power capability. One embodiment combines (in series or parallel) all four resistance elements 530 into a single low resistance high power bleed resistor. Resistance wire used to form resistor elements 530 may also be adjusted in gauge and length to achieve desired resistance and power capability. The grooves 512 in core 510 are sized according to the wire gauge used. The materials used for core 510 and base 520 are selected to withstand the operating temperature of the resistor elements 530. When installed on a printed circuit board the orientation of the resistor elements 530 are aligned with the magnetic field lines to minimize forces during magnetic pulses.

The advantages of the design shown in FIGS. 15A and 15B are:
1. Higher reliability—direct connection of the resistor elements into a printed circuit board eliminates a common point of failure for existing wire wound commercial resistors when used in high current pulse applications. Existing commercial resistors spot weld resistance wires to a metal cap; the metal cap is also welded to a lead that allows connection to a printed circuit board. This invention eliminates the metal cap, the additional leads and the spot welds found in existing products; the invention eliminates failure modes at the spot weld and in the areas right before the spot welds.
2. Higher accuracy—the resistance of power resistors as shown in FIGS. 15A and 15B depends solely on the length to the resistance wire; the elimination of the spot welds reduces resistance variation.
3. Compact size—the resulting size of the power resistor in FIGS. 15A and 15B can be smaller when compared to the volume required by using off-the-shelf resistors.

Figure 16:
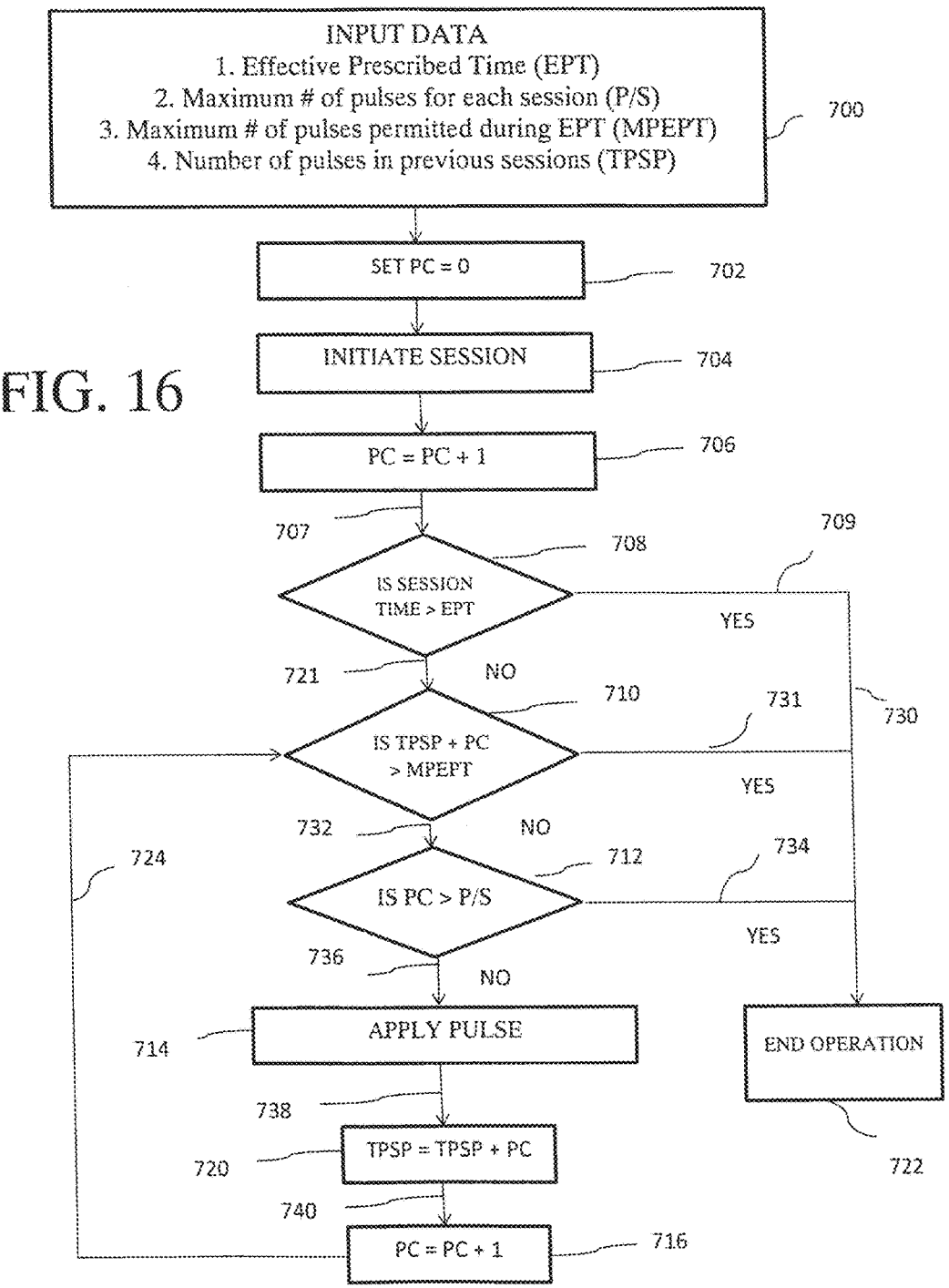
FIG. 16 is a computer logic flow diagram showing logic flow of the computer system operating the transcranial magnetic stimulation device.

Referring now to FIG. 16, there is shown a computer flow diagram for operational parameters of the TMS device 10. Initially, processor 699 is interfaced with SIM card 45 and is provided with input data such as (1) the effective prescribed time (EPT) which is the time limitations of the prescription given by a caregiver; (2) the maximum number of pulses for each sessions (P/S) which is part of the prescription given by the caregiver; (3) the maximum number of pulses per minute during some prescribed time given by the caregiver (MPEPT); and, (4) the total number of pulses provided in previous sessions (TPSP).

Initially, upon actuation of a control on/off button, TMS device 10 is placed in an operational mode. Computer 699 sets the pulse counts for the session (PC) equal to zero. The session is then initiated in logic block 704 and the pulse count (PC) of the current session is advanced by 1 in logic block 706.

Logic then passes on logic line 707 to decision block 708 where there is a determination of whether the session is being applied by the user within the effective prescribed time (EPT). If the session time is outside of the effective prescribed time provided by the caregiver, logic flows on lines and 730 to logic block 722 where the operation is ended and no pulse is delivered.

If the session time is less than the effective prescribed time (in other words, within the prescribed time) determined in decision block 708, logic flows on logic line 721 to decision block 710 where it is determined whether the total number of pulses for prior sessions and the pulse count for the current session is greater is greater than the maximum number of pulses prescribed during the effective prescribed time (EPT).

If the total number of pulses for prior sessions in addition to the pulse count of the current session is greater than the maximum number of pulses permitted (MPEPT) during the effective prescribed time (EPT), then the logic flows on lines 709 and 730 to end operation block 722 and once again no pulse is delivered to the user.

If the pulse count determined in logic block 710 is not greater than the maximum number of pulses permitted during the EPT, (MPEPT), then logic flows on logic line 732 into logic block 712 where it is determined whether the pulse count for the current session is greater than the maximum number of pulses allowed for each session (P/S). If the pulse count for the current session is greater than the maximum number of pulses allowed for each session, logic flows on lines 734 and 730 into end of operation block 722 and no pulse is delivered to the user.

If the pulse count of the current session (P/S) is not greater than the maximum number of pulses for a session (P/S), then logic flows on logic line 736 to block 714 where a pulse is applied.

Once the pulse is applied in accordance with a signal from logic block 714, the logic passes on logic line 738 to compute logic block 720 where the total number of pulses permitted during the effective prescribed time is updated by adding the pulse count for the current session (PC) to the number of pulses in previous sessions (TPSP).

Subsequent to updating in block 720, logic flows on logic line 740 to block 716 where the pulse count for the current session (PC) is increased by one. Logic then flows on line 724 to loop back to decision block 710 in preparation for a next pulse to be delivered.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed:

1. A transcranial magnetic stimulation (TMS) device for the treatment of neurological disorders, the TMS device including:
    at least one capacitor;
    a charging circuit to initiate the charging of the at least one capacitor placed within the TMS device in order to store electrical energy within the at least one capacitor;
    a magnetic coil having an inner section and an outer section, the magnetic coil having at least two turns of wire designed to deliver a magnetic pulse into the human body when the capacitor is discharged through the magnetic coil and, a magnetic custom bleed resistor within the TMS device includes at least one bleed resistor element formed from resistor wire wound on a core, said bleed resistor oriented within the TMS device to minimize forces applied to the bleed resistor by a magnetic pulse delivered by the TMS device, wherein said resistor wire is substantially aligned with magnetic field lines generated by said magnetic pulse.

2. The TMS device of claim 1 where the bleed resistor has 2 or more bleed resistor elements.

3. The TMS device of claim 2 where at least two of the bleed resistor elements are connected in parallel.

4. The TMS device of claim 2 where at least two of the bleed resistor elements are connected in series.

5. The TMS device of claim 1 further including a display including at least one display icon selected from the group of: prescription nearing the end, call customer service, temperature too high or low, charging progress, child lock, power connected, or battery charge level and combinations thereof.

6. The TMS device of claim 1 further including a receptacle for an insertable card having electronic memory containing a patient prescription, the prescription having an expiration date.

7. The TMS device of claim 1 further including a case adapted to be held by a patient on the portion of the case surrounding the capacitors.

8. The TMS device of claim 1 further including a visual display adapted to show the progress of device charging from initiation to completion.

9. The TMS device of claim 8 where the visual display is selected from the group including: a) a linear display of lights, b) a circular display of lights, c) an oval display of lights d) a rectangular display of lights or e) an elliptical display of lights.

10. The TMS device of claim 8 where the visual display is a sequence of LEDs.

* * * * *